(12) United States Patent
Averick et al.

(10) Patent No.: US 11,066,366 B2
(45) Date of Patent: Jul. 20, 2021

(54) HYDROPHILIC FENTANYL DERIVATIVES

(71) Applicant: Allegheny-Singer Research Institute, Pittsburgh, PA (US)

(72) Inventors: Saadyah Averick, Pittsburgh, PA (US); Ahmed Badr, Sewickley, PA (US); Shaohua Li, Pittsburgh, PA (US); Keith LeJeune, Export, PA (US)

(73) Assignee: Allegheny-Singer Research Institute, Pittsburgh, PA (US)

( * ) Notice: Subject to any disclaimer, the term of this patent is extended or adjusted under 35 U.S.C. 154(b) by 0 days.

(21) Appl. No.: 15/757,162

(22) PCT Filed: Sep. 6, 2016

(86) PCT No.: PCT/US2016/050398
§ 371 (c)(1),
(2) Date: Mar. 2, 2018

(87) PCT Pub. No.: WO2017/041095
PCT Pub. Date: Mar. 9, 2017

(65) Prior Publication Data
US 2018/0273475 A1 Sep. 27, 2018

Related U.S. Application Data

(60) Provisional application No. 62/214,004, filed on Sep. 3, 2015.

(51) Int. Cl.
| | | |
|---|---|---|
| C07D 211/58 | (2006.01) |
| C07D 401/10 | (2006.01) |
| C07F 9/59 | (2006.01) |
| C07D 405/12 | (2006.01) |
| C07D 401/14 | (2006.01) |
| C07D 401/06 | (2006.01) |

(52) U.S. Cl.
CPC .......... *C07D 211/58* (2013.01); *C07D 401/06* (2013.01); *C07D 401/10* (2013.01); *C07D 401/14* (2013.01); *C07D 405/12* (2013.01); *C07F 9/59* (2013.01)

(58) Field of Classification Search
CPC .................................................. C07D 211/58
USPC ........................................................ 546/224
See application file for complete search history.

(56) References Cited

U.S. PATENT DOCUMENTS

| | | |
|---|---|---|
| 5,053,411 A | 10/1991 | Bagley et al. |
| 7,056,500 B2 | 6/2006 | Bentley et al. |
| 8,349,307 B2 | 1/2013 | Bentley et al. |
| 8,778,322 B2 | 7/2014 | Seo et al. |
| 8,927,682 B2 | 1/2015 | Baker et al. |
| 2003/0105133 A1 | 6/2003 | Bigge et al. |
| 2010/0284960 A1 | 11/2010 | Riggs-Sauthier |
| 2011/0046180 A1 | 2/2011 | Peters et al. |
| 2011/0237614 A1 | 9/2011 | Jude-Fishburn et al. |
| 2013/0023553 A1 | 1/2013 | Jude-Fishburn et al. |
| 2015/0150999 A1 | 6/2015 | D'Souza et al. |

OTHER PUBLICATIONS

Liu, Pingwei et al., "Hyperbranched Polyethylenes Encapsulating Self-Supported Palladium(II) Species as Efficient and Recyclable Catalysts for Heck Reaction", Macromolecules, 2013, vol. 46, pp. 72-82.

Mukherjee, Nirmalya et al., "Solvent-free one-pot synthesis of 1,2,3-triazole derivatives by the "Click" reaction of alkyl halides or aryl boronic acids, sodium azide and terminal alkynes over a Cu/AL2O3 surface under ball-milling", Green Chemistry, 2013, 15, pp. 389-397.

*Primary Examiner* — Patricia L Morris
(74) *Attorney, Agent, or Firm* — Fox Rothschild LLP

(57) ABSTRACT

Various fentanyl derivatives are described. The derivatives exhibit high binding affinity to opioid receptors, but also have decreased blood brain permeability as compared to standard fentanyl. This, the resulting derivatives can be less addictive than standard fentanyl. Methods of making such derivatives are also disclosed in this document.

4 Claims, 17 Drawing Sheets

US 11,066,366 B2

HYDROPHILIC FENTANYL DERIVATIVES

RELATED APPLICATIONS AND CLAIM OF PRIORITY

This application is a U.S. national stage under 35 U.S.C. § 371 of International Patent Application No. PCT/US2016/050398, filed Sep. 6, 2016, which claims priority to U.S. provisional patent application number 62/214,004, titled "Hydrophilic fentanyl derivatives," filed Sep. 3, 2015, the disclosure of which is fully incorporated into this document by reference.

BACKGROUND

The treatment of pain and in particular chronic pain with opioid receptor agonists (for example, morphine, codeine, and fentanyl) is challenging and remains controversial due to the highly addictive nature and potential deadly side effects of these compounds. While opioids elicit their therapeutic effect by binding both central and peripheral receptors within the human nervous system and some soft tissues, the penetration of opioids across the blood-brain barrier (BBB) to bind to the brainstem neuronal receptors is the primary mechanism of opioid addiction. Additionally, the specific binding of an opioid to G protein-coupled receptors (GPCRs) within the brainstem causes unwanted analgesic side effects, including respiratory depression and death.

SUMMARY

This document identifies, in certain aspects, derivatives of fentanyl. In certain aspects, methods of making fentanyl derivatives are described.

In one embodiment, a method of synthesizing a derivative of fentanyl comprises reacting a fentanyl halide in the presence of a catalyst with a cross-coupling partner that comprises a terminal alkene or a terminal alkyne. The reacting may include adding a fentanyl halide, a solvent, and a base to a reaction chamber to which a cross-coupling partner is added. Oxygen may be removed from the reaction chamber by a process such as sparging. A catalyst such as palladium is added to the reaction chamber to form a mixture. After the mixture is mixed in the reaction chamber the catalyst is removed to yield the derivative of fentanyl.

In another embodiment, a method of synthesizing a derivative of fentanyl includes reacting a fentanyl azide with a terminal alkyne bearing compound in the presence of a copper catalyst. The reacting comprises dissolving the fentanyl azide in a solvent with a reactive partner bearing an alkyne group. Oxygen may be removed from the reaction chamber. A copper catalyst is added to the reaction chamber, and the reaction mixture is mixed to yield the derivative of fentanyl.

In another embodiment, a method of synthesizing a derivative of fentanyl comprises dissolving a fentanyl halide in a solvent to which a base has been added. Sodium azide is added to the reaction chamber to form a mixture. The mixture is refluxed in the reaction chamber for about 1 hour to about 12 hours to yield a reaction mixture. The reaction mixture is diluted with an organic solvent to yield a reaction layer. The reaction layer is then dried to form the derivative of fentanyl.

In another embodiment, a method of synthesizing a derivative of norfentanyl includes reacting a norfentanyl alkyne and an alkyne in the presence of copper. The norfentanyl alkyne is first prepared by treating the norfentanyl alkyne with azide in the presence of a copper catalyst. The prepared norfentanyl alkyne and add added to a reaction chamber that contains a solvent and abase. The mixture is mixed to form the norfentanyl derivative.

DETAILED DESCRIPTION

Figure 1:
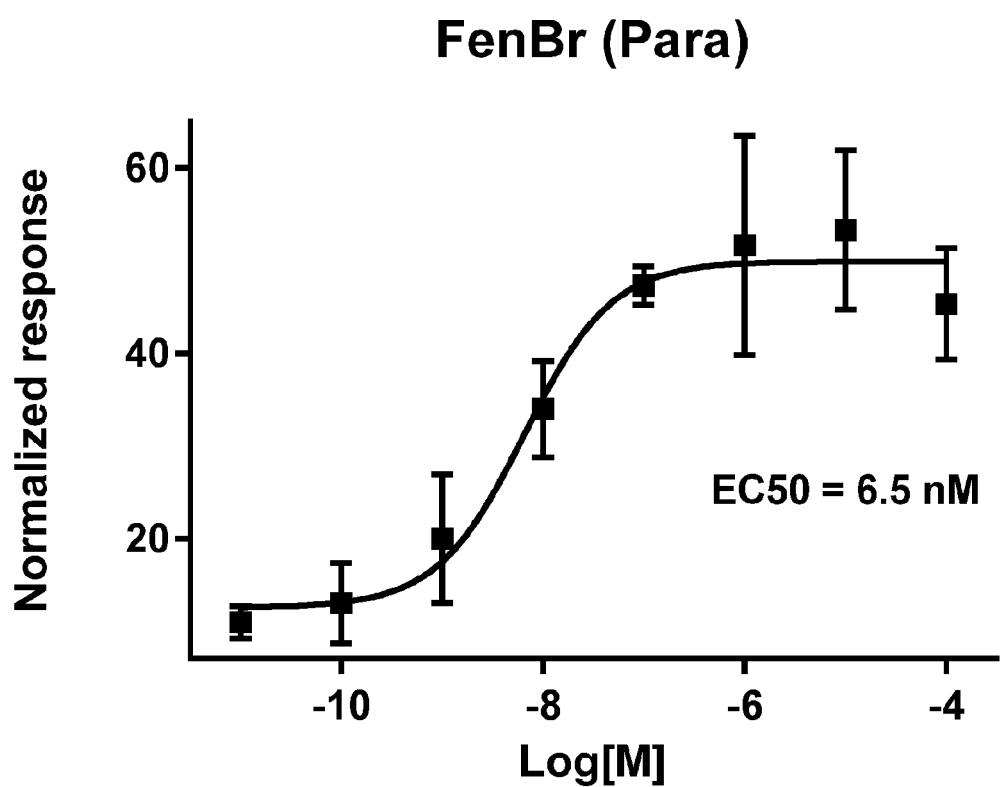
FIG. 1 shows the measurement of Fen-Br (para) dose-dependent cAMP inhibition in mu opioid receptor expressing CHO (Chinese hamster ovarian) cells.

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to."

This document described novel pain medications, components useful for making pain medications, and methods of making the medications and components. In various embodiments, these therapeutics may be used to inhibit pain while avoiding respiratory depression and the potential for addiction. For certain embodiments, the present inventors have designed derivatives of fentanyl (N-phenyl-N-[1-(2-phenylethyl)piperidin-4-yl]propanamide), imparted with functional groups to prevent/limit penetration through the blood brain barrier while still retaining a high affinity to opioid receptors, including, but not limited to, the μ-opioid receptor. The present inventors have also developed novel methods of making such derivatives.

In various embodiments, the compounds described, or made with the methods described, in this document have enhanced water solubility and polarity relative to fentanyl. Herein is described the chemical properties of the compounds that have been modified to enhance their water solubility and decrease potential blood brain barrier permeability.

There are three major molecular parameters that can be modified to enhance water solubility and diminish blood brain barrier permeability:

(1) Polar surface area (PSA): this parameter measures the number of polar heteroatoms (i.e., non-carbon) on a molecule. This document describes fentanyl derivatives having an increase in the number of polar atoms on the molecule. The derivatives prepared should have a predicted polar surface area greater than fentanyl 23.55, and in some embodiments greater than about 45.

(2) The calculated LogP (cLogP): this is the solubility coefficient of a compound in octanol vs. water. A lower cLogP indicates enhanced water solubility. The derivatives prepared should have a c Log P less than fentanyl's predicted cLogP of 3.79, and in some embodiments less than about 3.2.

(3) Molecular weight (MW). The described derivatives have increased molecular weights compared to fentanyl and are expected therefore to have decreased blood brain barrier permeability. The molecular weight of the derivatives should be greater than fentanyl's molecular weight of 336.48, and in some embodiments greater than about 415.

This document describes fentanyl derivatives with increased molecular weight, increased PSA and/or decreased cLogP, while retaining a high affinity for opioid receptors. In various examples, the inventors measured μ-opioid receptor affinity using a live cell assay with Chinese hamster ovarian cells (CHO) expressing the μ-opioid receptor (MOR). The molecular weight, PSA, and cLogP of the described derivatives were determined using ChemBioDraw Ultra.

Norfentanyl is a compound related to fentanyl with similar binding affinity to opioid receptors. In certain embodiments, the invention provides derivatives of norfentanyl, and particularly norfentanyl derivatives that have been modified to enhance their water solubility and decrease potential blood brain barrier permeability. In certain embodiments, the norfentanyl derivatives having an increase in the number of polar atoms on the molecule. In certain embodiments, the norfentanyl derivatives have a predicted polar surface area greater than norfentanyl, and in some embodiments greater than about 40. The norfentanyl derivatives may additionally have a cLogP less than norfentanyl's cLogP, and in some embodiments less than about 3.2. Additionally, the molecular weight of the norfentanyl derivatives should be greater than norfentanyl's molecular weight, and in some embodiments greater than about 400.

In certain embodiments, the present disclosure provides fentanyl derivatives having a "ridged" linking group pendant to the fentanyl. These fentanyl derivatives may be prepared using the palladium catalyzed cross coupling of terminal alkenes and alkynes with fentanyl halides. Other cross coupling groups may include, but are not limited to, acrylates, methacrylates, styrenics, methacrylamides, acrylamides, and alkynes. These derivatives have yielded promising lead compounds.

In other embodiments, the present disclosure provides Cu(I) catalyzed azide-alkyne cycloaddition between fentanyl-azide derivatives (Fen-$N_3$) and alkyne bearing compounds.

In other embodiments, the present disclosure provides Cu(I) catalyzed azide-alkyne cycloaddition between norfentanyl-alkyne derivatives (Norfen-Alkyn) and azide bearing compounds.

The derivatives described in this document may fulfill unmet needs in the treatment of pain and the management of chronic pain, while preventing addiction and many of the troubling side-effects of opioid therapeutics.

Embodiment 1: Fentanyl Derivatives Having High PSA and/or c Log P

In certain embodiments, the methods described in this document may yield fentanyl derivatives according to Formula Ia or Formula Ib below:

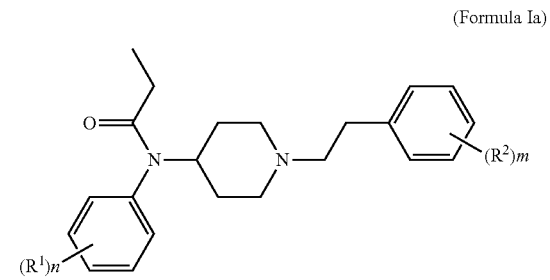

(Formula Ia)

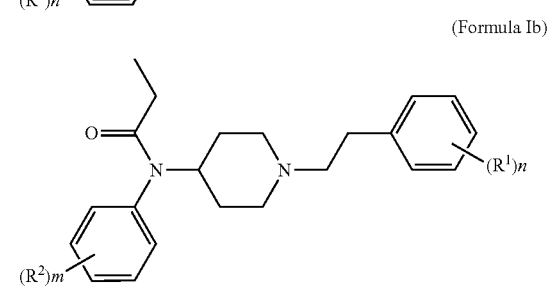

(Formula Ib)

wherein:
each $R^1$ is independently selected from the group consisting of halo, hydroxyl, lower alkyl, amino, carboxyl, and trifluoromethyl;
n is 0, 1 or 2;
m is 1 or 2;
$R^2$ is $-(L)_x-R^3$, in which:
x is 0 or 1;
L is a linking group;
$R^3$ is selected from the group consisting of:
(a) $-(CH_2)_e-Y$,
(b) $-(CH_2)_f-CR^{31}R^{32}-(CH_2)_g-Y$, and
(c) $-X^1-X^2-Z$,
in which:
e is a number from 0 to 6; f is a number from 1 to 4;
g is a number from 1 to 4;

$R^{31}$ is OH or $NH_2$, $R^{32}$ is H or lower alkyl, or alternatively $R^{31}$ and $R^{32}$ are taken together with the carbon to which they are attached to form a 4- to 6-membered ring having from 0 to 2 heteroatom ring members;

$X^1$ is selected from the group consisting of —C(=O)—, and —$(CH_2)_p$— wherein p is a number from 1 to 8;

$X^2$ is selected from the group consisting of —S—, —O—, and —NH—; and

Y is selected from the group consisting of H, OH, halo, —$NR_2$, —S(=O)$CH_3$, —$SO_2$—$CH_3$, —$SO_2NR_2$, —$PO_3R^2$, ammonium, phosphonium, sulfonium, guaninidinium, sulfate, carboxylate, alkyl, aryl, heteroaryl, aralkyl, cycloalkyl, heterocyclic alkyl, oligomer, polymer, and a zwitterionic group;

Z is either (a) selected from the group consisting of H, amino, alkyl, aryl, heteroaryl, aralkyl, cycloalkyl, oligomer and a polymer; or Z is, or (b) a group of the formula —$(CH_2)_h$—$Z^1$, wherein h is from 1 to 6 and $Z^1$ is halo, OH, —$NR_2$, —S(=O)$CH_3$, —$SO_2$—$CH_3$, —$SO_2NR_2$, —$PO_3R^2$, ammonium, phosphonium, sulfonium, guaninidinium, sulfate, carboxylate, pyridinium, aryl, heteroaryl, heterocyclic alkyl and a zwitterionic group; and each R is independently selected from H and methyl.

In some variations of these embodiments, the fentanyl derivatives have one or more of the following properties: (i) a predicted polar surface area greater than 23.55, and more preferably greater than about 45; (ii) a c Log P less than 3.79, and more preferably less than about 3.2; and (iii) a molecular weight of greater than 336.48, and in some embodiments greater than about 415. In some embodiments, the fentanyl derivatives have two of the properties selected from (i), (ii) and (iii) above. In other embodiments, the fentanyl derivatives have each of the properties (i), (ii) and (iii) above.

In some embodiments, the fentanyl derivative comprises one or more hydrophilic polar and/or charged substituents, which are part of the structure of $R^3$. The polar or charged substituent(s) may be selected from the following group: —OH, —$NR_2$, —S(=O)$CH_3$, —$SO_2$—$CH_3$, —$SO_2NR_2$, —$PO_2R^3$, ammonium, phosphonium, sulfonium, guaninidinium, sulfate, phosphate, carboxylate, heteroaryl, heterocyclic alkyl, oligomer, polymer, and a zwitterionic group, wherein each R is independently selected from H and methyl. Various hydrophilic groups that may be used in these embodiments include:

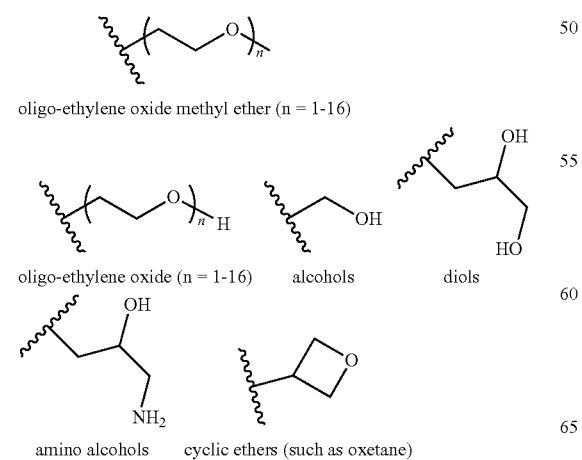

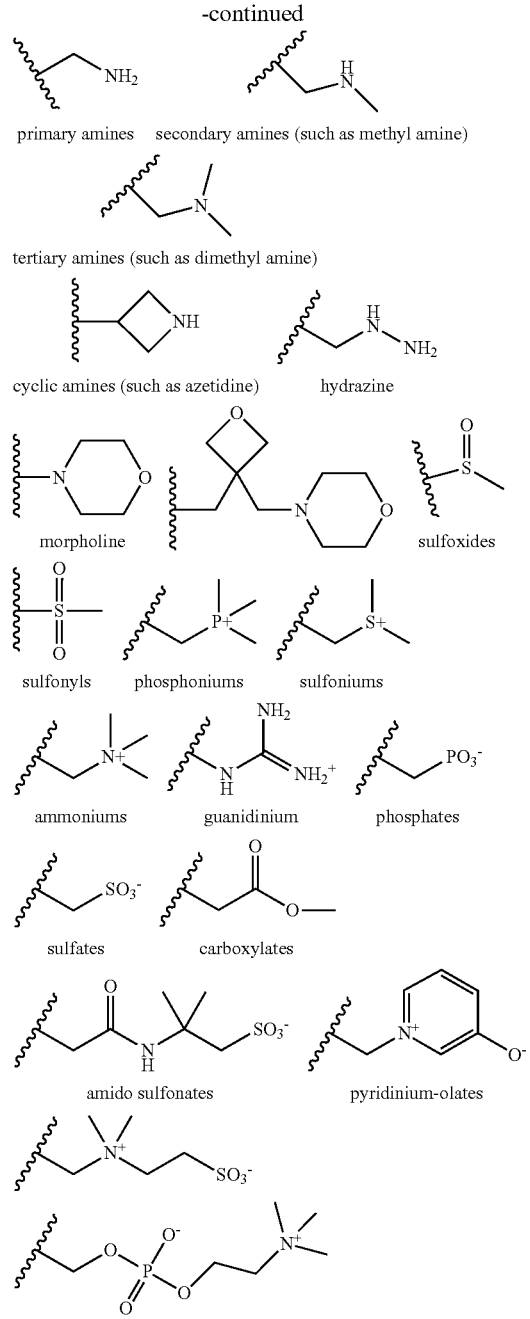

In certain embodiments, the fentanyl derivative may have Formula Ic or Formula Id below:

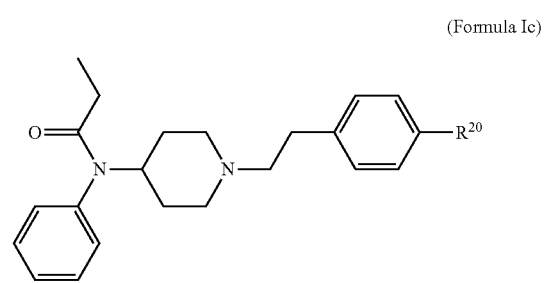

(Formula Ic)

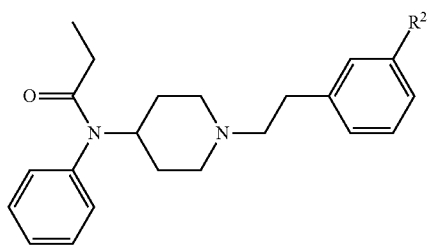

(Formula Id)

wherein:

R²⁰ is selected from the group consisting of OH, halo, —NR₂, —S(═O)CH₃, —SO₂—CH₃, —SO₂NR₂, —PO₃R², ammonium, phosphonium, sulfonium, guaninidinium, sulfate, carboxylate, heteroaryl, heterocyclic alkyl, and a zwitterionic group; and each R is independently selected from H and lower alkyl.

The fentanyl derivatives may be prepared by substitution reactions starting with for example fentanyl halide. Alternatively, the fentanyl derivative may be prepared by designing blocks with functionalized phenyl groups and incorporating them into a fentanyl derivative, according, for example, the following schemes:

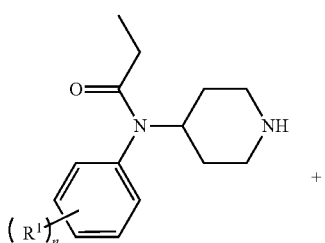

+

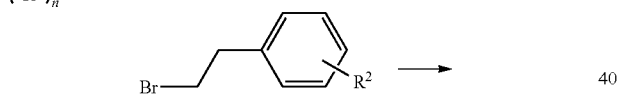

→

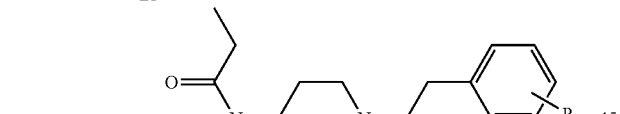

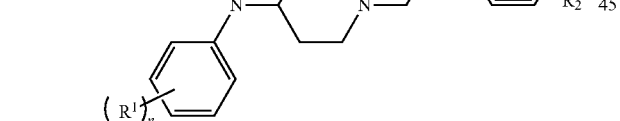

+

→

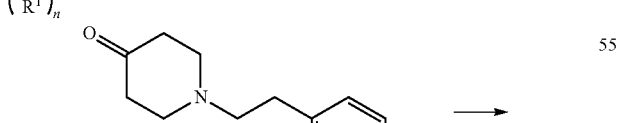

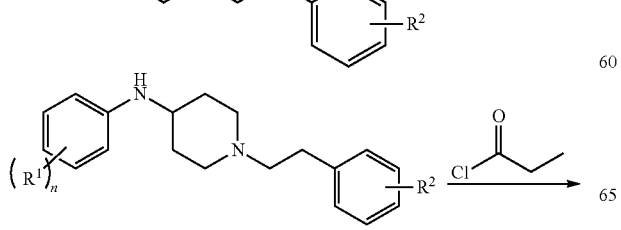

In other embodiments, the fentanyl derivative may be prepared by treating a fentanyl-OSO₂F with an amine having the formula HNR₂:

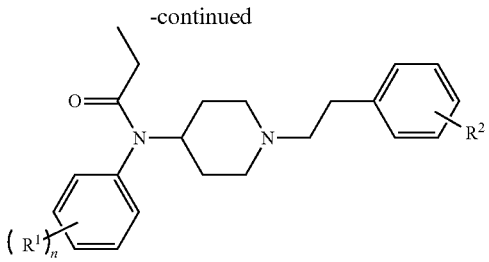

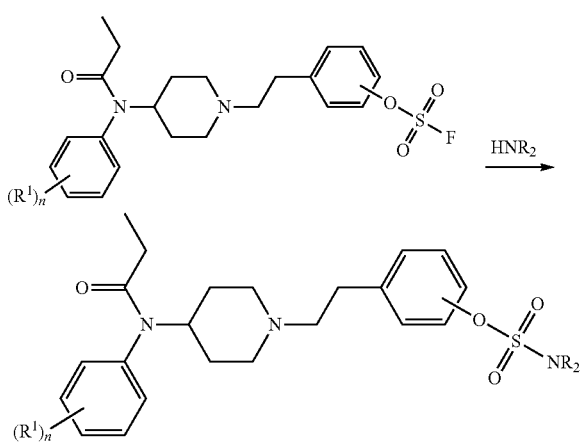

wherein each R is independently selected from H and methyl, whereby an exchange occurs between the fluoride and the amine.

Embodiment 2: Fentanyl Derivatives with Ridged Linking Groups

Certain embodiments provide fentanyl derivatives according to Formula IIa or Formula IIb below:

(Formula IIa)

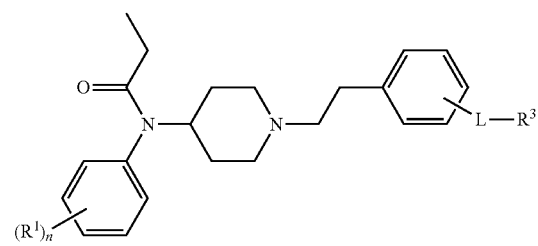

(Formula IIb)

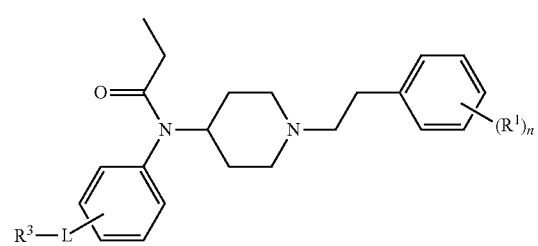

wherein:
each $R^1$ is independently selected from the group consisting of halo, hydroxyl, lower alkyl, amino, carboxyl, and trifluoromethyl;
n is 0, 1 or 2;
L is a linking group;
$R^3$ is selected from the group consisting of:
(a) —$(CH_2)_e$—Y,
(b) —$(CH_2)_f$—$CR^{31}R^{32}$—$(CH_2)_g$—Y, and
(c) —$X^1$—$X^2$—Z,
in which:
e is 1 to 6; f is 1 to 4; g is 1 to 4;
$R^{31}$ is OH or $NH_2$; $R^{32}$ is H or lower alkyl, or alternatively $R^{31}$ and $R^{32}$ are taken together with the carbon to which they are attached to form a 4- to 6-membered ring having from 0 to 2 heteroatom ring members;
$X^1$ is selected —C(=O)— or —$(CH_2)_p$— wherein p is 1 to 8;
$X^2$ is selected from the group consisting of —S—, —O—, and —NH—;
Y is selected from the group consisting of H, OH, halo, —$NR_2$, —S(=O)$CH_3$, —$SO_2$—$CH_3$, —$SO_2NR_2$, —$PO_3R^2$, ammonium, phosphonium, sulfonium, guaninidinium, sulfate, phosphate, carboxylate, alkyl, aryl, heteroaryl, aralkyl, cycloalkyl, heterocyclic alkyl, oligomer, polymer, and a zwitterionic group;
Z is either (a) selected from the group consisting of H, amino, alkyl, aryl, heteroaryl, aralkyl, cycloalkyl, oligomer and a polymer, or (b) a group of the formula —$(CH_2)_h$—$Z^1$, wherein h is a number from 1 to 6 and $Z^1$ is selected from the group consisting of OH, halo, —$NR_2$, —S(=O)$CH_3$, —$SO_2$—$CH_3$, —$SO_2NR_2$, —$PO_3R^2$, ammonium, phosphonium, sulfonium, guaninidinium, sulfate, phosphate, carboxylate, pyridinium, aryl, heteroaryl, heterocyclic alkyl and a zwitterionic group; and
each R is independently selected from H and methyl.

In certain embodiments, the linking group L provides a "ridged" unit or spacer. In such embodiments, L may be selected from the group consisting of —(CH=CH)$_a$—, —(CH=CR)$_b$—, —C≡C—, and —CH=CH—Ar—, wherein:
a is 1, 2 or 3;
b is 1, 2 or 3;
Ar is an aryl or heteroaryl group; and
each R is independently selected from H and methyl.

In certain embodiments, the use of a rigid linking group between the fentanyl and the hydrophilic moiety allows the derivative compound to retain its ability to activate the mu opioid receptor and subsequently prevent the sensation of pain in animal models, while increasing molecular weight and/or hydrophilicity of the derivative compounds. In some embodiments, hydrophilicity may be less than about 3.2, increased molecular weight may be greater than about 415, and increases in polar surface are greater than about 45.

In some embodiments, the fentanyl derivative comprises one or more hydrophilic polar and/or charged substituents, which are part of the structure of $R^3$ as provided above.

In some embodiments, the oligomer or polymer (Y, Z or Z) is a hydrophilic, water soluble oligomer or polymer. For example, the oligomer/polymer may be a polyethylene glycol polymer having up to 20 monomer units, and in some embodiments up to 16 monomer units. In certain embodiments, the polyethylene glycol has the formula —($CH_2CH_2$—O)$_m$—H or —($CH_2CH_2$—O)$_m$—$CH_3$, wherein m is from 1 to 16. In other embodiments, the oligomer or polymer may be polylactic acid, polyglycolic acid, or co-polymers thereof. In certain embodiments, the oligomer or polymer may have the formula —(CO—CHR—O)$_m$H, wherein R is H or methyl, and m is from 1 to 16. Other polymers include acrylates, methacrylates, acrylamides, methacrylamides, styrenics and copolymers thereof. In certain embodiments, the oligomer may comprise one or more polar and/or charged groups, as described above, that are pendant to the backbone.

In certain embodiments, the fentanyl derivatives may have one of the following structures:

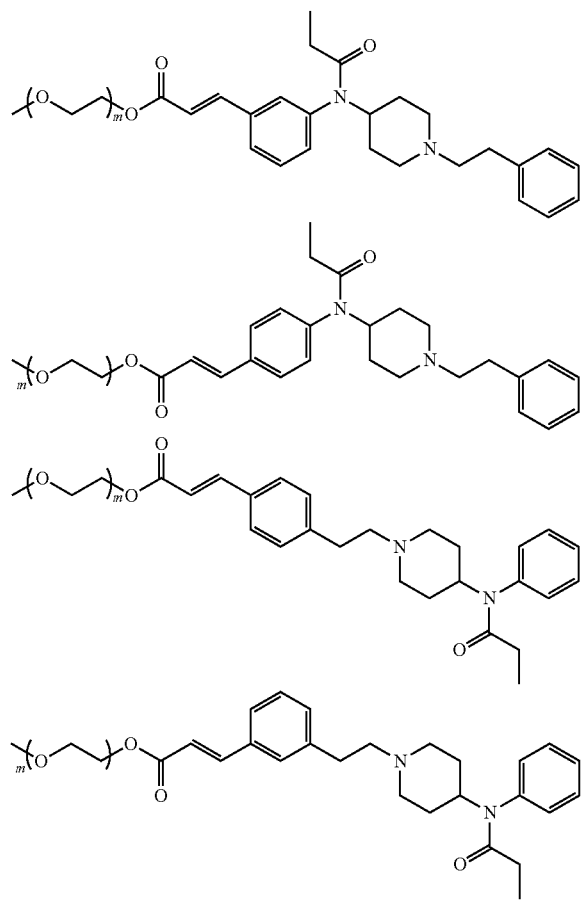

wherein m is a number from 1 to 16.

In certain embodiments, fentanyl derivatives may be prepared from a fentanyl halide or a fentanyl pseudo-halide by a cross coupling reaction in the presence of a catalyst according to the process of Schemes Ia to Id:

Scheme Ia

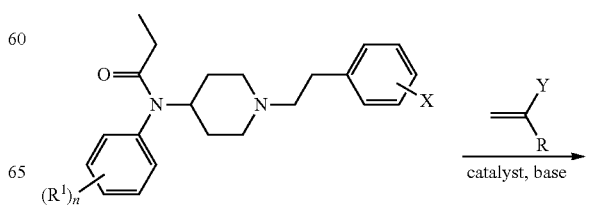

-continued

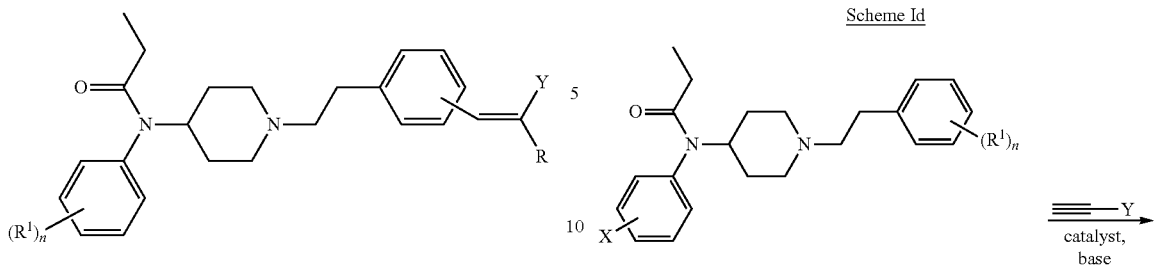

Scheme Ib

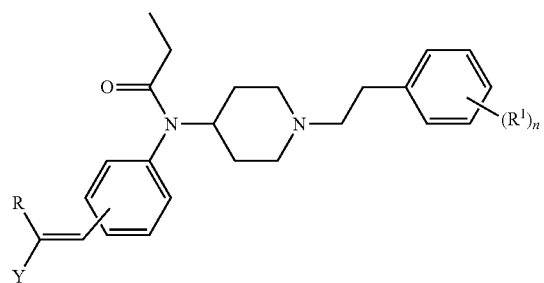

Scheme Ic

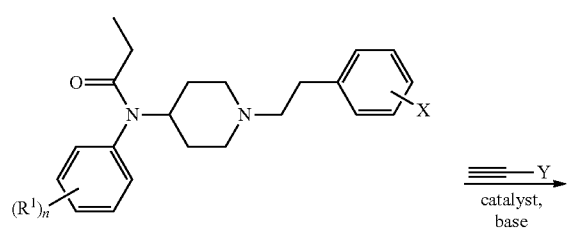

Scheme Id

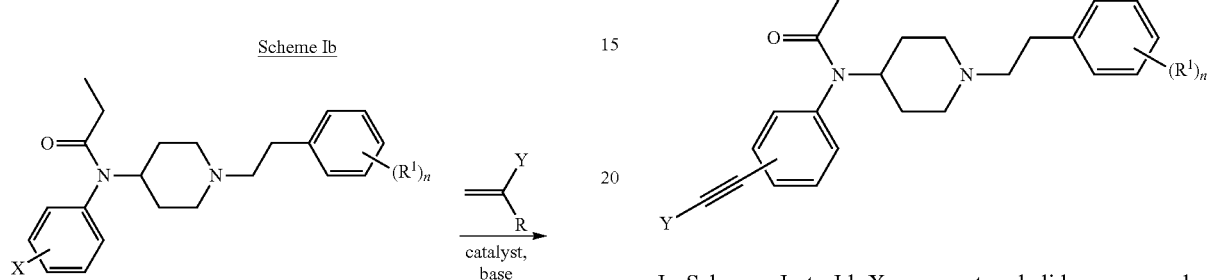

In Schemes Ia to Id, X represents a halide or a pseudo-halide, and in some embodiments may be selected from Cl, Br, I and —OTf (triflate). The substituent Y is any group of interest compatible with a cross-coupling reaction. In some embodiments for Schemes Ia and Ib, X is in the meta or para position. Each $R_1$ is independently selected from the group consisting of halo, hydroxyl, lower alkyl, amino, carboxyl, and trifluoromethyl; while n is 0, 1 or 2.

In some embodiments of the process according to Schemes Ia to Id, a fentanyl halide derivative is dissolved in an organic solvent, for example a polar aprotic solvent, in a reaction chamber. A base is added to the solvent. The base can be a tertiary amine or inorganic base. The coupling partner ($H_2C$=CRY or HC≡C—Y) is added and oxygen is removed from the reaction chamber, for example by sparging with an inert gas such as nitrogen or argon. A transition metal catalyst is added (e.g., a palladium based catalyst) and the reaction mixture is stirred or otherwise mixed. The mixing may occur, and the reaction time may vary, for example from about 16 to about 96 hours, and in some embodiments may be about 50 to about 72 hours. The reaction mixture is then diluted with an organic solvent that is immiscible with water such as dichloromethane and extracted with water. The catalyst can be removed using a neutral alumina column, extracted into the aqueous phase, or precipitated. The product can be isolated as a free base or precipitated from an organic solvent as an acid salt.

The fentanyl derivatives, such as fentanyl halide/pseudo-halide, may be prepared by designing blocks with aryl halide functional groups and incorporating them into a fentanyl derivative, according, for example, to the following schemes:

Scheme II

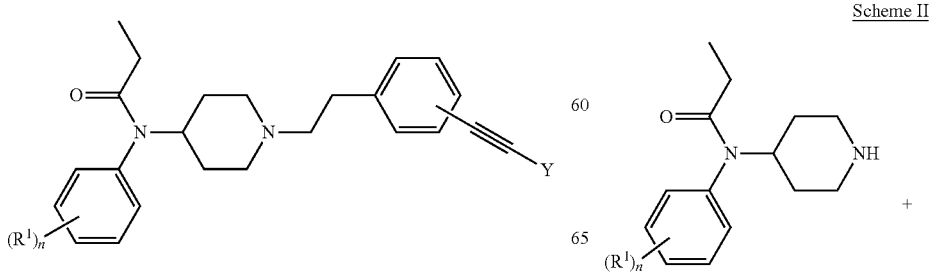

-continued

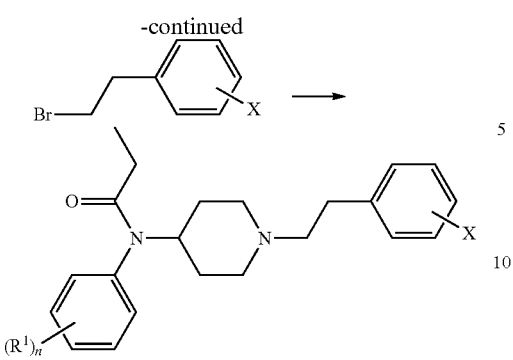

Scheme III

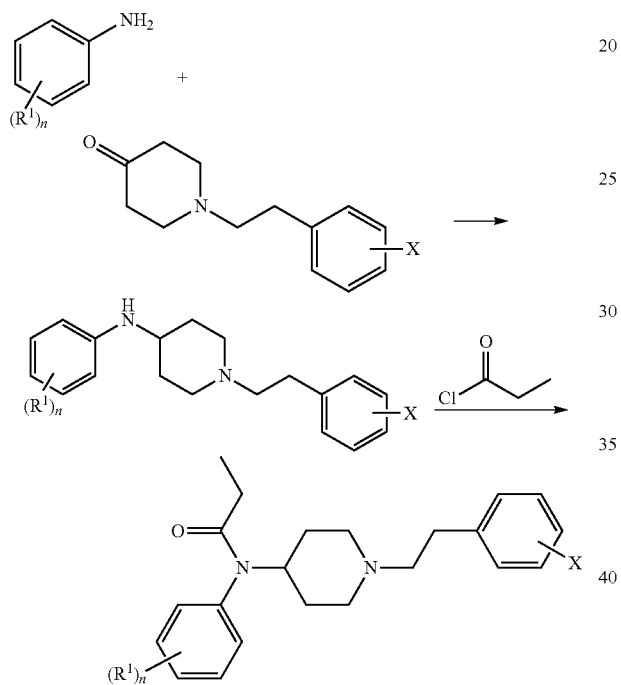

In certain embodiments, the coupling partner (H$_2$C=CRY or HC≡C—Y), has the formula HL-X$^1$—X$^2$—Z$^0$, wherein:
L is selected from the group consisting of —(CH=CH)$_a$—, —(CH=CR)$_b$—, and —C≡C—;
each R is independently selected from H and CH$_3$;
a is 1, 2 or 3;
b is 1, 2 or 3;
X$^1$ is selected from the group consisting of —C(=O)—, and —(CH$_2$)$_p$— wherein p is 1 to 8;
X$^2$ is selected from the group consisting of —S—, —O—, and —NH—; and
Z$^0$ is Z (as defined above in the context of Formulae Ia and Ib) or is a chemical precursor used to form Z.
In other embodiments, the coupling partner (H$_2$C=CRY or HC≡C—Y), has the formula HL-(CH$_2$)$_e$—Y$^0$; or HL-(CH$_2$)$_f$—CR$^{31}$R$^{32}$—(CH$_2$)$_g$—Y$^0$; wherein L, R, e, f, g, R$^{31}$ and R$^{32}$ are defined as provided above. Y$^0$ is Y (as defined above in the context of Formulae IIa and IIb), or is a chemical precursor used to form Y.
In certain embodiments the coupling partner is selected from the group consisting of:

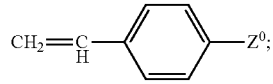

H$_2$C=CH—Z$^0$; HC≡C—Z$^0$; H$_2$C=CR—C(=O)—O—Z$^0$; H$_2$C=CR—C(=O)—NH—Z$^0$; H$_2$C=CR—C(=O)—NR—Z$^0$; and

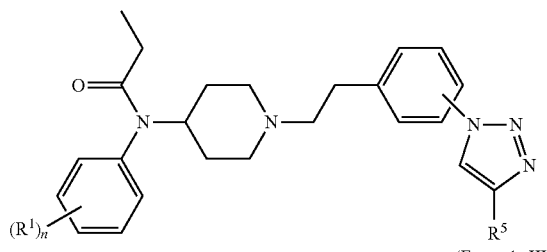

wherein each R is independently selected from H or methyl, and Z$^0$ is Z (as defined above in the context of Formulae Ia and Ib) or is a chemical precursor used to form Z.

The catalyst used in the coupling reaction may be any transition metal catalyst used in Heck or Sonagashira coupling reactions. Examples of such catalysts utilize palladium (II) as the transition metal.

Embodiment 3: Copper Catalyzed Fentanyl-Azide Cycloaddition with Alkynes

Certain embodiments provide fentanyl derivatives according to Formula IIIa or Formula IIIb:

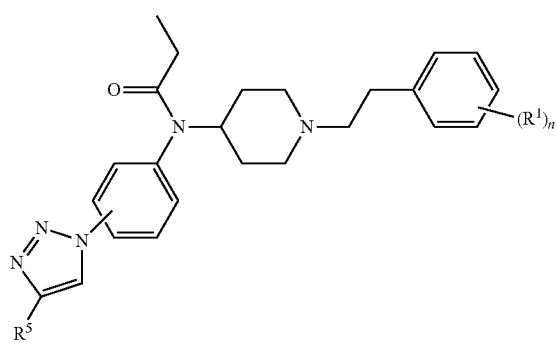

wherein:
each R$^1$ is independently selected from halo, hydroxyl, lower alkyl, amino, carboxyl, and trifluoromethyl;
n is selected from 0, 1 or 2;
R$^5$ has the formula —(CH$_2$)$_c$—(X$^3$)$_d$—Z$^2$, wherein:
c is from 1 to 16;
d is 0 or 1;
X$^3$ is —O— or —NR—;
Z$^2$ is selected from the group consisting of H, OH, —NR$_2$, —S(=O)CH$_3$, —SO$_2$—CH$_3$, —SO$_2$NR$_2$, —PO$_3$R$^3$, ammonium, phosphonium, sulfonium, guaninidinium, sulfate, phosphate, carboxylate, alkyl, aryl, heteroaryl, aralkyl, cycloalkyl, heterocyclic alkyl, oligomer, polymer, and a zwitterionic group; and
each R is independently selected from H and methyl.

In some embodiments for compounds of Formulae IIIa and IIIb, the triazole is bonded at the meta or para position of the adjacent phenyl group.

In certain embodiments, the polymer is a hydrophilic, water soluble polymer as described above.

In certain embodiments, the fentanyl derivative has one of the following structures:

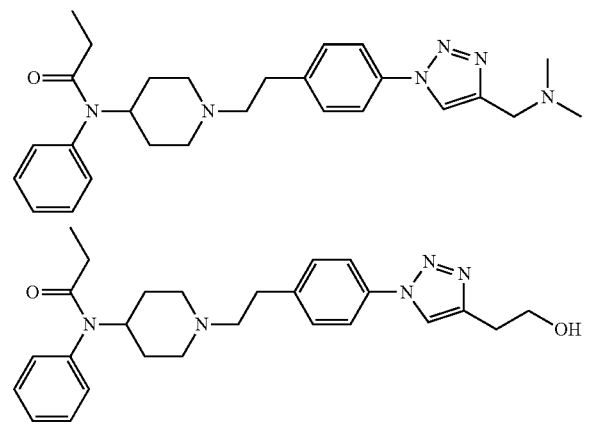

In certain embodiments, fentanyl derivatives may be prepared from a fentanyl azide by a cyclo-addition reaction with an alkyne in the presence of a copper catalyst according to the following schemes:

Scheme IVa

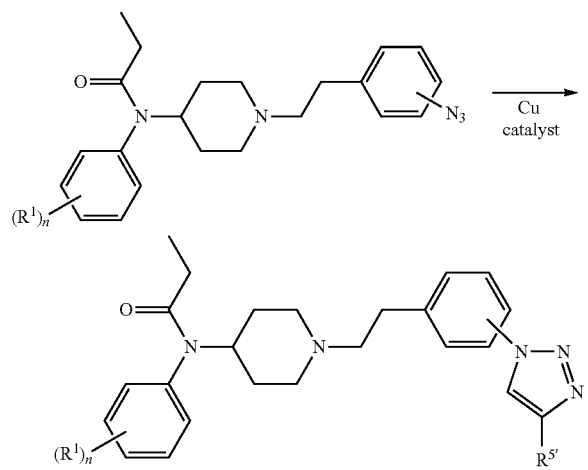

Scheme IVb

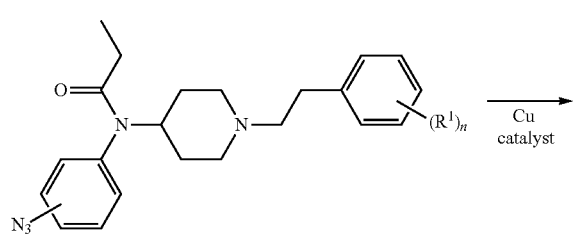

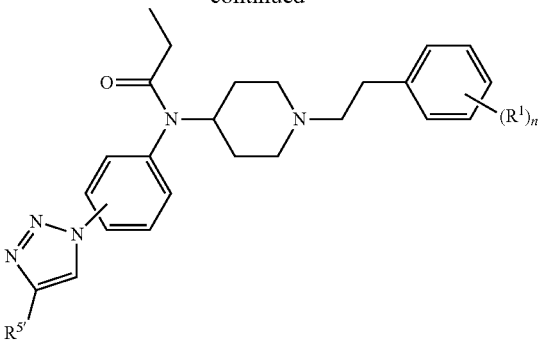

In each of these schemes, R, $R^1$ and have the definitions set forth above in the context of Formulae IIIa and IIIb. $R^{5'}$ is $R^5$ (as defined above in the context of Formulae IIIa and IIIb) or is a chemical precursor used to form $R^5$.

In some embodiments for Schemes IVa and IVb, the azide group $N_3$ is in the meta or para position.

In some embodiments of processes according to Schemes IVa and IVb, a fentanyl azide derivative is dissolved in a suitable solvent in a reaction chamber and mixed with a stoichiometric equivalent or excess of an reactive partner bearing an alkyne group (HC≡C—$R^{5'}$). The reaction mixture may be sparged with an inert gas to remove oxygen. Copper, and in some cases Cu(I), between 0.1-5% by mole is added to the reaction mixture and the reaction is stirred or otherwise mixed between 1- and 48 hours. The reaction mixture is then diluted with an organic solvent immiscible with water such as dichloromethane and extracted with water. The Cu(I) catalyst can be removed using a neutral alumina column, extracted into the aqueous phase, or precipitated. The product can be isolated as a free base or precipitated from an organic solvent as an acid salt.

The fentanyl-azide derivative can be prepared from a fentanyl halide. The fentanyl halide is dissolved in an aqueous alcohol solution (such as ethanol). Copper (I) and a tertiary amine base are dissolved in an oxygen free aqueous alcohol solution, such as ethanol and water (v/v=7:3). Oxygen may be removed by sparging with an inert gas. The fentanyl halide, sodium azide and sodium are then added to the reaction mixture and the solution is refluxed for 1 to 12 hours, for example about 3 hours, to prevent the reduction of fentanyl azide to fentanyl amine. The reaction mixture is then diluted with an organic solvent immiscible with water such as dichloromethane and extracted with water. The organic layer is then washed with base, water, and brine. The organic layer is then dried under vacuum to afford the fentanyl azide.

The alkyne used in the cycloaddition reaction is a terminal alkyne or a strained cyclic alkyne. In certain embodiments, a terminal alkyne with the formula HC≡C—$(CH_2)_c$—$Z^3$ is used, wherein: c is from 1 to 16; $Z^3$ is selected from the group consisting of OH, —$NR_2$, —S(=O)$CH_3$, —$SO_2$—$CH_3$, —$SO_2NR_2$, —$PO_3R^3$, and carboxylate; and each R is independently selected from H and methyl.

The catalyst for the cycloaddition reaction may be a Cu(I) catalyst. In the cases of strained alkynes, no catalysis is required for the azide-alkyne cycloaddition.

Embodiment 4: Copper Catalyzed Norfentanyl-Azide Cycloaddition with Alkynes

Certain embodiments provide norfentanyl derivatives according to Formula IV:

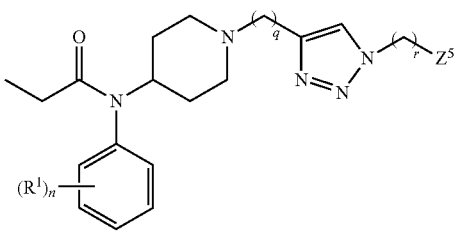

(Formula IV)

wherein:
each $R^1$ is independently selected from the group consisting of halo, hydroxyl, lower alkyl, amino, carboxyl, and trifluoromethyl;
n is 0, 1 or 2;
q is from 1 to 12;
r is from 1 to 16;
$Z^5$ is either (a) selected from the group consisting of H, OH, $-NR_2$, $-S(=O)CH_3$, $-SO_2-CH_3$, $-SO_2NR_2$, $-PO_3R^2$, ammonium, phosphonium, sulfonium, guanidinium, sulfate, phosphate, carboxylate, alkyl, aryl, heteroaryl, aralkyl, cycloalkyl, heterocyclic alkyl, oligomer, polymer, and a zwitterionic group; or (b) a group formula $-X^4-Z^6$, in which:
  $X^4$ is selected from the group consisting of $-O-$, $-S-$, and $-NR-$; and
  $Z^6$ is selected from the group consisting of H, alkyl, aryl, heteroaryl, cycloalkyl, heterocyclic alkyl, oligomer, a polymer and a zwitterionic group;
each R is independently selected from H and methyl.

Compounds of Formula IV may be prepared from norfentanyl, or a derivative thereof, according to the following scheme:

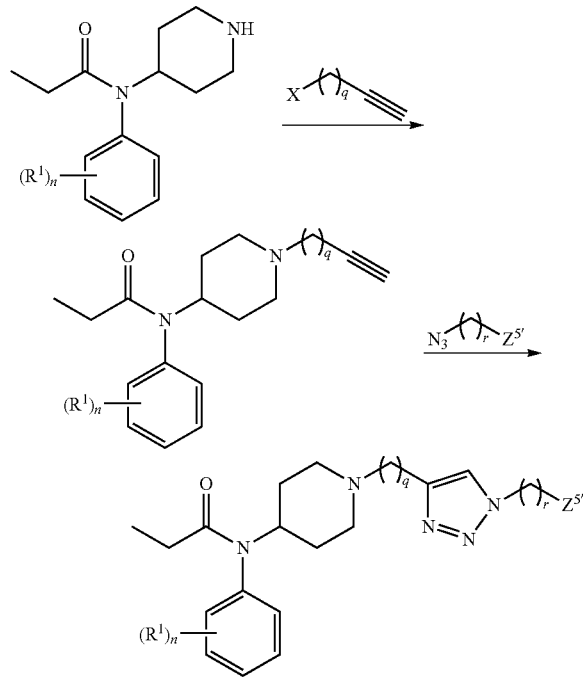

in which the $R^1$s and n are as described above, and $Z^{5'}$ is $Z^5$ or is a chemical precursor used to form $Z^5$.

In the above scheme, a norfentanyl derivative and a base are dissolved in an organic solvent or solvents, such as polar aprotic solvents. The base may be, for example, a tertiary amine. An alkyne alkyl halide, $X-(CH_2)_q-C\equiv CH$, is added, optionally with cooling (X is a halide such as Br or I, or a pseudohalide such as $-OTf$). The reaction may be stirred at 0° C. for 1 hour, and then at room temperature for 24 hours. The resulting norfentanyl-alkyne product may be isolated according to standard techniques.

The norfentanyl triazole derivative is then prepared by treating the norfentanyl-alkyne with an excess (1.1 to 10) of an azide in the presence of a copper (such as Cu(I)) catalyst with at least 0.1% (e.g., about 5%) loading. The product may be purified using precipitation or column chromatography.

The azide used in the cycloaddition reaction may be a terminal azide, $N_3-(CH_2)_r-Z^{5'}$. In certain embodiments, the terminal azide has the formula $N_3-(CH_2)_r-Z^6$; wherein r is 1 to 16; $Z^6$ is selected from the group consisting of OH, $-NR_2$, $-S(=O)CH_3$, $-SO_2-CH_3$, $-SO_2NR_2$, $-PO_3R^3$, and carboxylate; and each R is independently selected from H and methyl.

As used herein, the term "alkyl" refers to the radical of saturated aliphatic groups, including straight-chain alkyl groups and branched-chain alkyl groups. In some embodiments, a straight chain or branched chain alkyl has 1 to 12 carbon atoms, and in some embodiments 1 to 6 carbon atoms. The term "lower alkyl" refers to alkyl groups having from 1 to three carbon atoms.

The term "cycloalkyl" refers to saturated, carbocyclic groups having from 3 to 7 carbons in the ring. Examples of cycloalkyl groups include cyclopropyl, cyclobutyl, cyclopentyl and cyclohexyl.

The term "aralkyl", as used herein, refers to an alkyl group substituted with an aryl group (e.g., an aromatic or heteroaromatic group).

The term "aryl" as used herein includes 5- and 6-membered single-ring aromatic groups that may include from zero to three heteroatoms, for example, benzene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be unsubstituted or can be substituted at one or more ring positions with halogen, alkyl, cycloalkyl, hydroxyl, alkoxyl, amino, nitro, carboxyl, $-CF_3$, $-CN$, or the like.

The term "heterocyclic alkyl" refers to non-aromatic cyclic groups having 3 to 6 ring members with 2 to 5 ring carbons and from 1 to 3 ring heteroatoms. Examples of heterocyclic alkyl groups include morpholine, oxetane, azetidine, tetrahydrofuran, tetrahydropyran, thiolane, pyrrolidine, piperidine, and the like.

The term "heteroatom" as used herein means an atom of any element other than carbon or hydrogen. Examples of heteroatoms that may be used in various embodiments include are nitrogen, oxygen, and sulfur.

The term "ammonium" as used herein refers to a positively charged nitrogen group bonded to four carbon atoms. Example of ammonium groups have the formula $-N^+(R^0)_3$, wherein each $R^0$ is independently selected from a lower alkyl group.

The term "phosphonium" as used herein refers to a positively charged phosphorus atom bonded to three carbon atoms. Examples of phosphonium groups have the formula $-P^+(R^0)_3$, wherein each $R^0$ is independently selected from a lower alkyl group.

The term "sulfonium" as used herein refers to a positively charged sulfur group bonded to three carbon atoms. Examples of sulfonium groups have the formula —S+(R⁰)₂, wherein each R⁰ is independently selected from a lower alkyl group.

A zwitterionic group as used herein is a substituent group that contains both a positively charged group and a negatively charged group. The positively charged group may be an ammonium, sulfonium, phosphonium, guanidinium, or the like, and the negatively charged group may be a phosphate, sulfate, carboxylate, or the like. Examples of zwitterionic groups include the following structures:

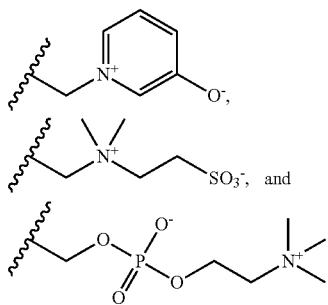

Various compounds provided for in this document contain a basic amine functional group, and are thus capable of forming pharmaceutically-acceptable salts with pharmaceutically-acceptable acids. The term "pharmaceutically-acceptable salts" in this respect, refers to relatively non-toxic, inorganic and organic acid addition salts of compounds described in this document. Representative salts include the hydrochloride, hydrobromide, sulfate, bisulfate, phosphate, nitrate, acetate, palmitate, stearate, laurate, benzoate, lactate, tosylate, citrate, maleate, fumarate, succinate, tartrate, napthylate, mesylate, and the like. (See, for example, Berge et al. (1977) "Pharmaceutical Salts", J. Pharm. Sci. 66:1-19).

Certain compounds provided for in this document may contain an acidic functional group, and are thus capable of forming pharmaceutically-acceptable salts with pharmaceutically-acceptable bases. Representative salts include metal salts such as sodium, potassium, and the like, and ammonium salts (See, for example, Berge et al. (1977).

The compounds described in this document or resulting from processes described in this document may be used in method of treating pain in a patient in need of such treatment. In such methods, a therapeutically effective amount of any of the compounds described in this document or resulting from processes described in this document is provided to the patient.

In another aspect, pharmaceutically acceptable compositions may include a therapeutically-effective amount of one or more of the compounds described in this document or resulting from processes described in this document, formulated together with one or more pharmaceutically acceptable carriers (additives) and/or diluents. Such pharmaceutical compositions may be specially formulated for administration in solid or liquid form, including those adapted for the following: (1) oral administration, for example, tablets and capsules; (2) parenteral administration, for example, by subcutaneous, intramuscular, or intravenous injection as, for example, a sterile solution or suspension; (3) transdermally, for example, as a patch applied to the skin; (4) sublingually; or (5) nasally.

The phrase "therapeutically-effective amount" as used herein means that amount of a compound which is effective for producing the desired therapeutic effect, i.e., reduction in pain experience by the patient, with a reasonable benefit/risk ratio applicable to any medical treatment, e.g., reasonable side effects.

The following abbreviations have the following meanings in the examples below:
CHO=Chinese hamster ovarian
DMF=Dimethylformamide
DBU=1,8-Diazabicyclo[5.4.0]undec-7-ene
Et₃N=triethylamine
PPh₃=Triphenylphosphine
Pd(OAc)₂=Palladium(II) acetate
rt=room temperature
TBAF—Tetra-n-butylammonium fluoride
TPMA—Tris(2-pyridylmethyl)amine The following examples illustrate how specific fentanyl derivatives may be produced.

In various experiments, the inventors have found that dose dependent measurement of an opioid receptor agonist's ability to inhibit cAMP production in a Forskolin-stimulated mu opioid receptor expressing cell-lines indicated an agonist ability to activate the mu opioid receptor. The lower the 50% inhibitory concentration achieved for a compound indicates that lower amounts of compound are required to produce an analgesic effect in animal and human models of pain.

A hot plate withdrawal latency test measured the amount of time required to induce a withdrawal event (jumping or hind paw licking) in animal placed on a hot plate (heated to 55° C. for example) up to a predetermined maximum time (30 seconds for example). The greater the time duration an animal can endure on a hot plate indicates the strength of analgesia induced by the given compound. The lower the concentration of a compound required to achieve masking of pain the more potent an analgesic effect the compound exerts on a molar concentration basis.

EXAMPLES

Example 1

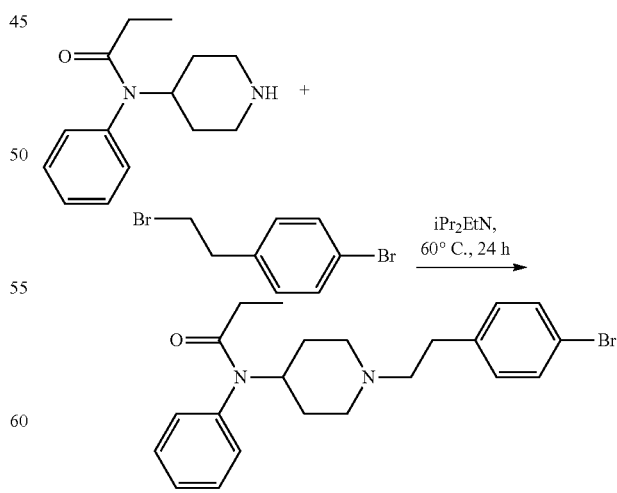

Fen-Br

Fen-Br: N-phenyl-N-piperidin-4-yl-propionannide (Norfentanyl, 0.93 g, 4.0 mmol) and 4-bromophenethyl bromide (1.58 g, 6.0 mmol) were dissolved in 15 mL DMF, followed by addition of N,N-diisopropylethylamine (0.78 g, 6.0 mmol). The reaction was kept stirring at 60° C. for 24 hours. The reaction mixture was cooled to room temperature before ethyl ether (100 mL) was added, and the organics were washed with 1 N NaOH (30 mL×3), water (30 mL×3) and brine (30 mL×3). The organics were then dried over MgSO$_4$ and concentrated under vacuum. The organics were redissolved in ethyl ether, and pure Fen-Br were precipitated as HCl salt by addition of HCl in ethanol solution (95%). $^1$H NMR (500 MHz, CDCl$_3$): δ 7.41-7.35 (m, 5H), 7.08 (dd, J=8.5, 8.5 Hz, 2H), 7.02 (d, J=8.5 Hz, 2H), 4.68 (tt, J=12.0, 4.0 Hz, 1H), 3.00 (d, J=12.0 Hz, 2H), 2.67 (m, 2H), 2.53 (m, 2H), 1.96 (dd, J=15.0, 7.5 Hz, 2H), 1.80 (d, J=13.0 Hz, 2H), 1.6-1.4 (m, 4H), 1.03 (t, J=7.5 Hz, 3H).

FIG. 1 illustrates the measurement of Fen-Br (para) dose-dependent cAMP inhibition in mu opioid receptor expressing CHO (Chinese hamster ovarian) cells.

Example 2

Fen-Acrylates: Fen-Br (270 mg, 0.6 mmol) and acrylates (6 mmol, 10 eq) were dissolved in Et$_3$N (2 mL) and DMF (3 mL). Pd(PPh$_3$)$_2$Cl$_2$ (2.1 mg, 0.003 mmol) was added, and the reaction was kept stirring at 140° C. under N$_2$ overnight. The reaction mixture was cooled to room temperature before dichloromethane (100 mL) was added, and the solution was passed through a neutral alumina column to remove the Pd catalyst. The mixture was washed with 1 M NaOH, water and brine, and was dried over MgSO$_4$. The organics were concentrated under vacuum, and redissolved in ether. Crude product was precipitated by addition of HCl in ethanol, and the precipitate was further purified by column chromatography (1:2 Hexane/ethyl acetate) to afford the desired product.

Example 3

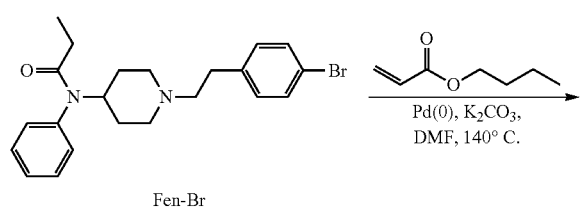

Fen-Br

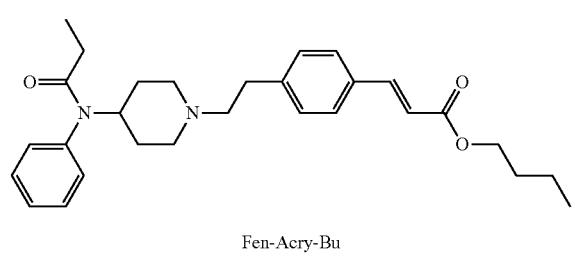

Fen-Acry-Bu

Fen-Acry-Bu was prepared according to the conditions provided in Example 2: (90%). $^1$H NMR (500 MHz, CDCl$_3$): δ 7.66 (d, J=16.0 Hz, 1H), 7.45-7.39 (m, 5H), 7.18 (d, J=7.0 Hz, 2H), 7.10 (dd, J=8.5, 8.5 Hz, 2H), 6.40 (d, J=16.0 Hz, 1H), 4.70 (tt, J=12.0, 4.0 Hz, 1H), 4.22 (t, J=5.0 Hz, 2H), 3.00 (d, J=12.0 Hz, 2H), 2.76-2.60 (m, 2H), 2.52 (td, J=12.0, 1.5 Hz, 2H), 2.19-2.15 (m, 2H), 1.96 (dd, J=15.0, 7.5 Hz, 2H), 1.82 (d, J=13.0 Hz, 2H), 1.70 (q, J=7.0 Hz, 2H), 1.45 (m, 2H). 1.46 (q, J=12.0 Hz, 2H), 1.03 (t, J=7.5 Hz, 3H), 0.96 (t, J=7.0 Hz, 3H).

Figure 2:
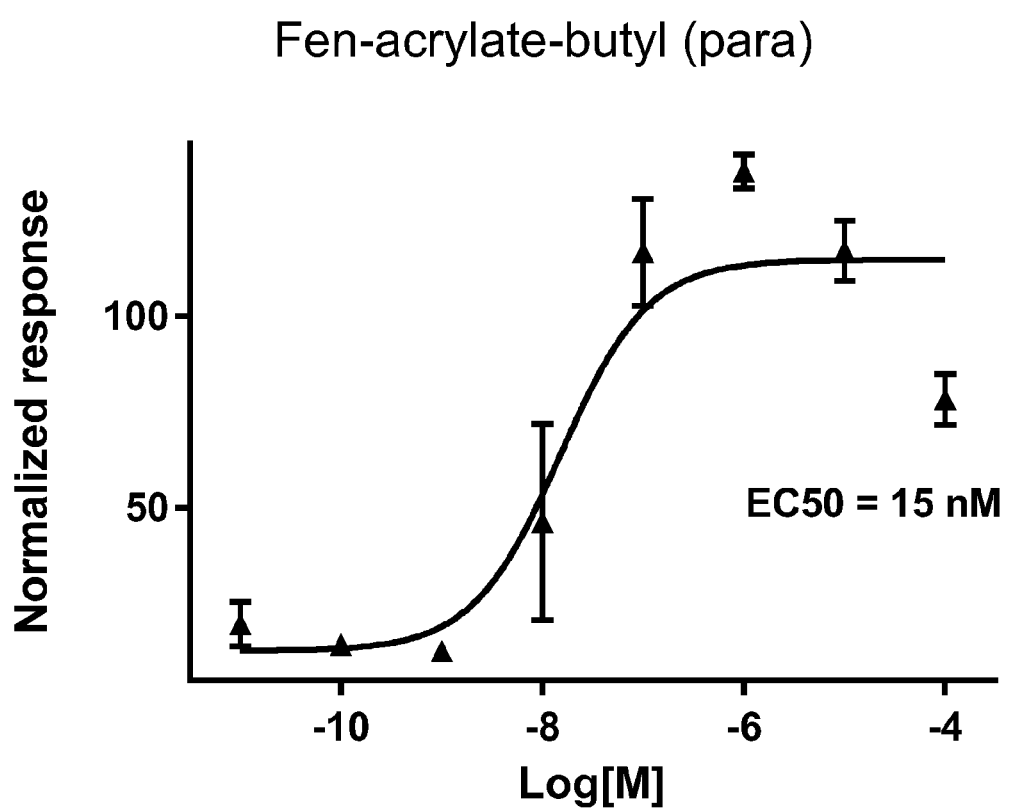
FIG. 2 shows the measurement of Fen-acrylate-butyl (para) dose-dependent cAMP inhibition in mu opioid receptor expressing CHO (Chinese hamster ovarian) cells.

FIG. 2 illustrates the measurement of Fen-acrylate-butyl (para) dose-dependent cAMP inhibition in mu opioid receptor expressing CHO (Chinese hamster ovarian) cells.

Example 4

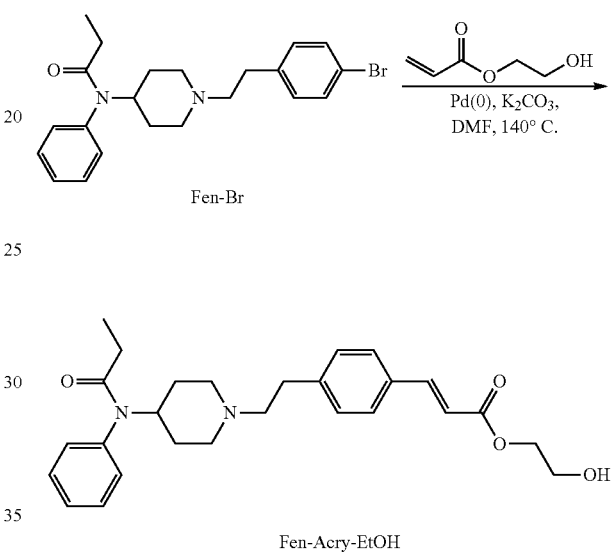

Fen-Acry-EtOH

Fen-Acry-EtOH was prepared according to the conditions provided in Example 2: (85%). $^1$H NMR (500 MHz, CDCl$_3$): δ 7.69 (d, J=16.0 Hz, 1H), 7.45-7.39 (m, 5H), 7.24 (d, J=7.0 Hz, 2H), 7.11 (dd, J=8.5, 8.5 Hz, 2H), 6.44 (d, J=16.0 Hz, 1H), 4.81 (tt, J=12.0, 4.0 Hz, 1H), 4.35 (t, J=5.0 Hz, 2H), 3.90 (t, J=5.0 Hz, 2H), 3.63 (d, J=12.0 Hz, 2H), 3.23 (m, 2H), 3.14 (m, 2H), 2.84 (td, J=12.0, 1.5 Hz, 2H), 2.2-1.9 (m, 6H), 1.02 (t, J=7.5 Hz, 3H).

Figure 5:
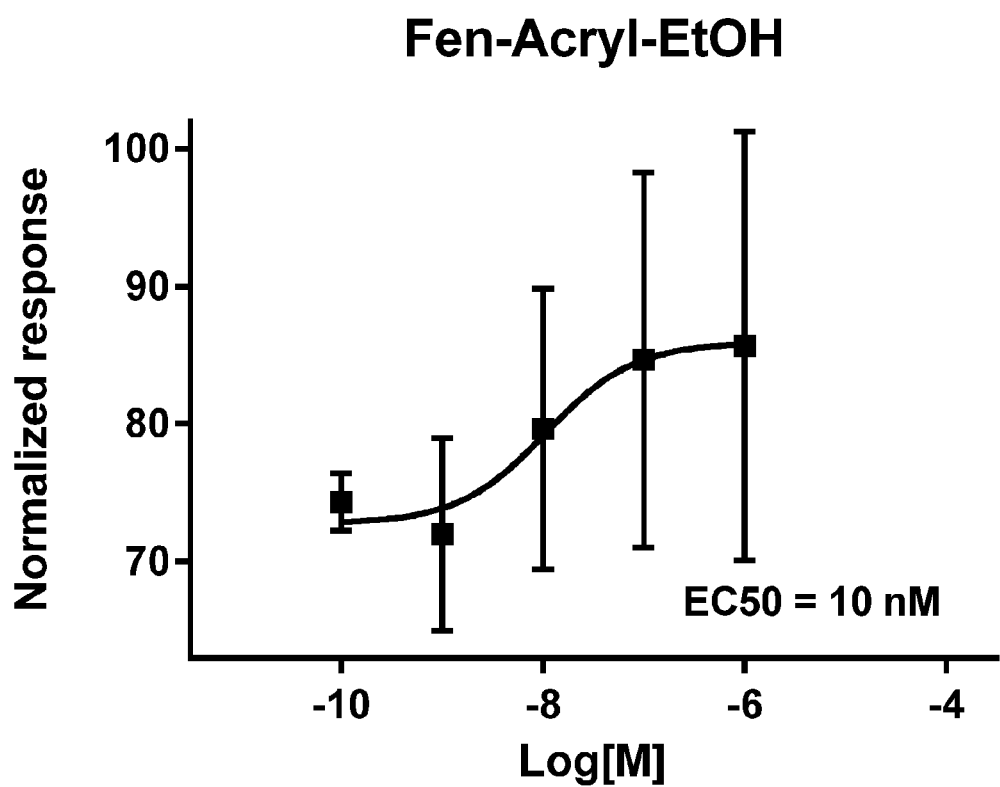
FIG. 5 shows the measurement of Fen-acrylate-EtOH (ethanol) (para) dose-dependent cAMP inhibition in mu opioid receptor expressing CHO (Chinese hamster ovarian) cells.

FIG. 5 illustrates measurement of Fen-acrylate-EtOH (ethanol) (para) dose-dependent cAMP inhibition in mu opioid receptor expressing CHO (Chinese hamster ovarian) cells Example 5

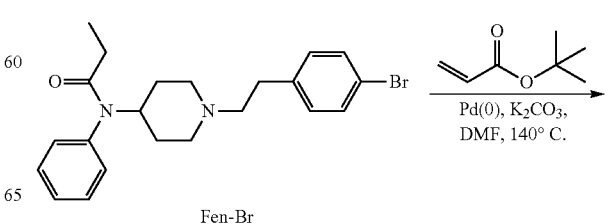

Fen-Br

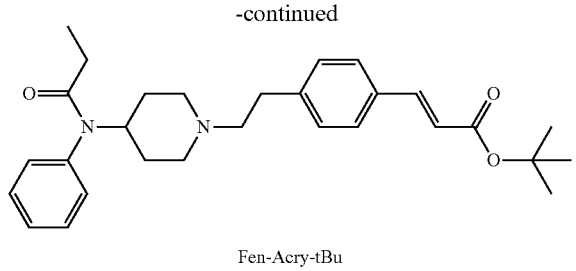

Fen-Acry-tBu

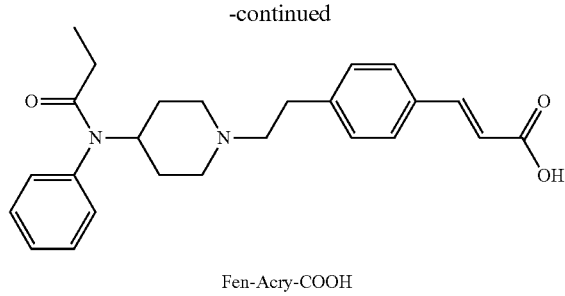

Fen-Acry-COOH

Fen-Acry-tBu was prepared according to the conditions provided in Example 2: (75%). $^1$H NMR (500 MHz, CDCl$_3$): δ 7.66 (d, J=16.0 Hz, 1H), 7.45-7.39 (m, 5H), 7.18 (d, J=7.0 Hz, 2H), 7.10 (dd, J=8.5, 8.5 Hz, 2H), 6.40 (d, J=16.0 Hz, 1H), 4.71 (tt, J=12.0, 4.0 Hz, 1H), 3.00 (d, J=12.0 Hz, 2H), 2.76-2.60 (m, 2H), 2.52 (td, J=12.0, 1.5 Hz, 2H), 2.19-2.15 (m, 2H), 1.96 (dd, J=15.0, 7.5 Hz, 2H), 1.82 (d, J=13.0 Hz, 2H), 1.55 (s, 9H), 1.46 (q, J=12.0 Hz, 2H), 1.03 (t, J=7.5 Hz, 3H).

Example 6

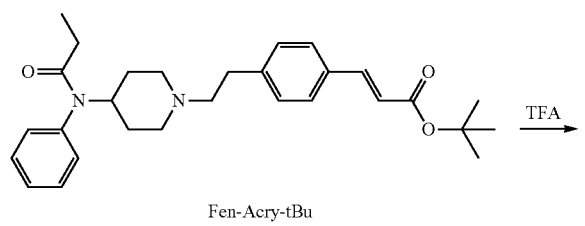

Fen-Acry-tBu

To prepare Fen-Acry-COOH, Fen-Acry-tBu (270 mg, 0.6 mmol) was dissolved in dichloromethane (20 mL) with slow addition of trifluoroacetic acid (1 mL). The solution was stirred at room temperature for 24 hours. 1 N HCl (40 mL) was added, and the reaction mixture was extracted with dichloromethane (20 mL) three times. The organics were combined, washed with water and brine, and was evaporated under high vacuum to afford pure Fen-Acry-COOH (95%). $^1$H NMR (500 MHz, CDCl$_3$): δ 7.56 (d, J=16.0 Hz, 1H), 7.5-7.4 (m, 5H), 7.26 (d, J=7.0 Hz, 2H), 7.12 (dd, J=8.5, 8.5 Hz, 2H), 6.36 (d, J=16.0 Hz, 1H), 4.82 (tt, J=12.0, 4.0 Hz, 1H), 3.65 (d, J=12.0 Hz, 2H), 3.27 (m, 2H), 3.14 (m, 2H), 2.84 (td, J=12.0, 1.5 Hz, 2H), 2.2-1.9 (m, 6H), 1.04 (t, J=7.5 Hz, 3H).

Figure 6:
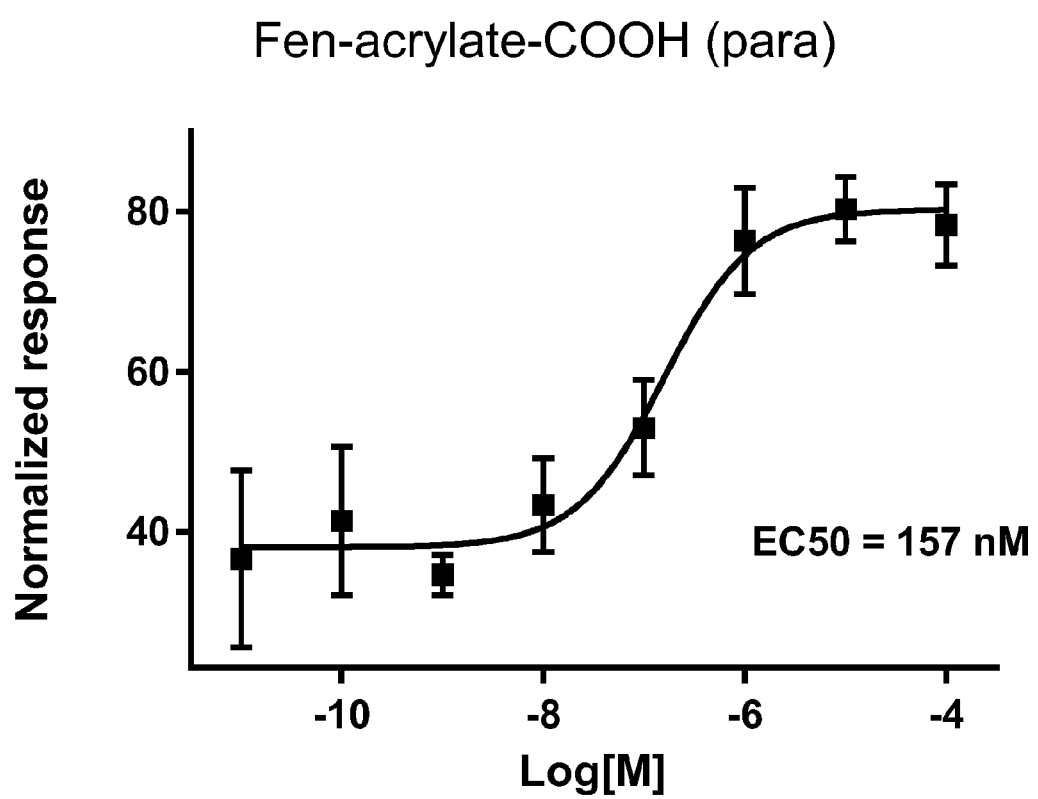
FIG. 6 shows the measurement of Fen-acrylate-COOH (para) dose-dependent cAMP inhibition in mu opioid receptor expressing CHO (Chinese hamster ovarian) cells.

FIG. 6 illustrates measurement of Fen-acrylate-COOH (para) dose-dependent cAMP inhibition in mu opioid receptor expressing CHO (Chinese hamster ovarian) cells Example 7

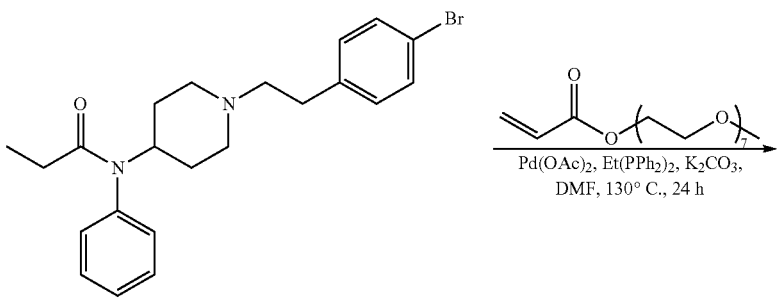

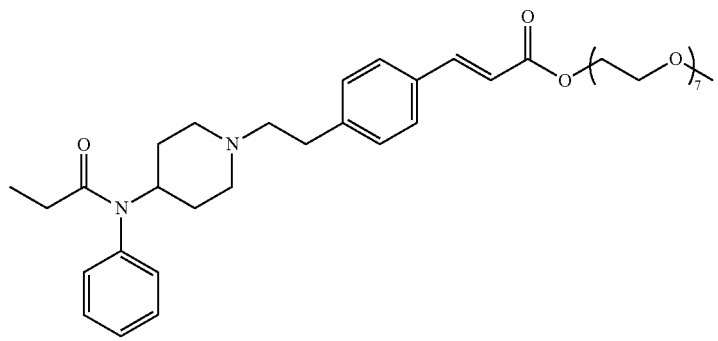

Fen-Acry-PEO7 was prepared according to the conditions provided in Example 2: (56%). $^1$H NMR (500 MHz, CDCl$_3$): δ 7.67 (d, J=16.0 Hz, 1H), 7.52-7.45 (m, 5H), 7.28 (d, J=7.0 Hz, 2H), 7.11 (dd, J=8.5, 8.5 Hz, 2H), 6.46 (d, J=16.0 Hz, 1H), 4.82 (tt, J=12.0, 4.0 Hz, 1H), 4.38 (t, J=5.0 Hz, 2H), 3.68 (t, J=5.0 Hz, 2H), 3.65-3.60 (m, 24H), 3.56 (m, 2H), 3.40 (s, 3H), 3.27 (d, J=12.0 Hz, 2H), 3.12 (s, 2H), 2.84 (td, J=12.0, 1.5 Hz, 2H), 2.19 (m, 2H), 2.00 (dd, J=15.0, 7.5 Hz, 2H), 1.96 (d, J=13.0 Hz, 2H), 1.04 (t, J=7.5 Hz, 3H).

Figure 4:
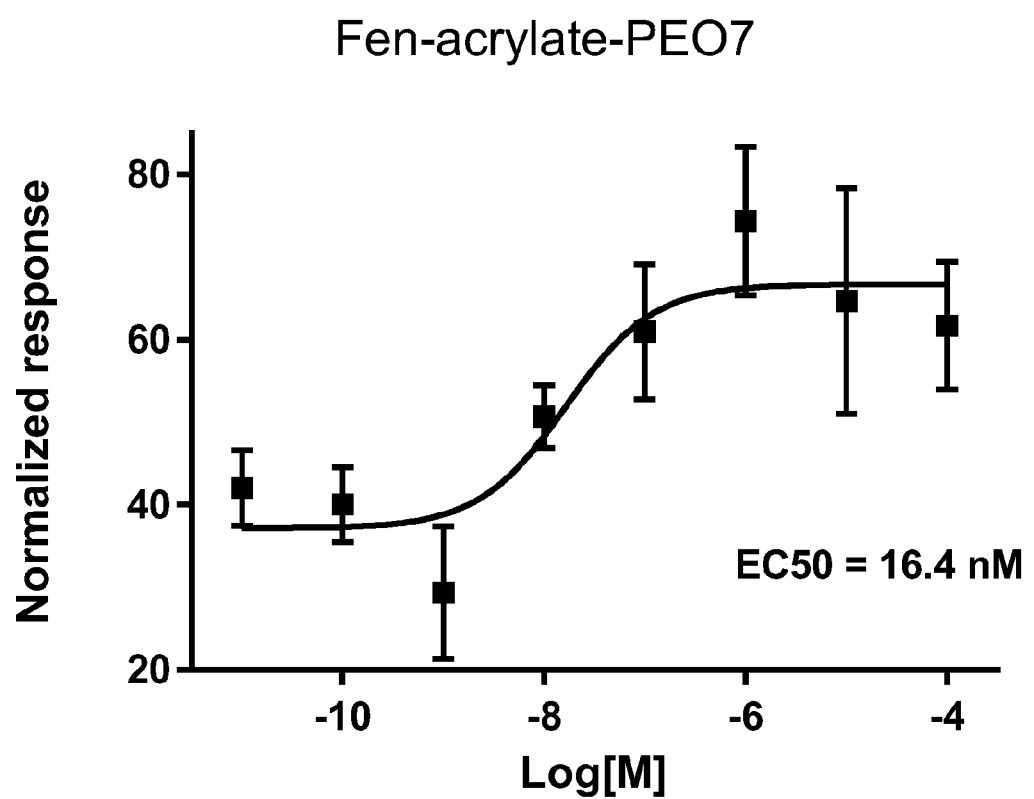
FIG. 4 shows the measurement of Fen-acrylate-PEO7 (para) dose-dependent cAMP inhibition in mu opioid receptor expressing CHO (Chinese hamster ovarian) cells.

FIG. 4 illustrates the measurement of Fen-acrylate-PEO7 (para) dose-dependent cAMP inhibition in mu opioid receptor expressing CHO (Chinese hamster ovarian) cells.

Example 8

Fen-Acry-PEO9 was prepared according to the conditions provided in Example 2: (70%). 1H NMR (500 MHz, CDCl3): δ 7.68 (d, J=16.0 Hz, 1H), 7.45-7.39 (m, 5H), 7.18 (d, J=7.0 Hz, 2H), 7.10 (dd, J=8.5, 8.5 Hz, 2H), 6.44 (d, J=16.0 Hz, 1H), 4.70 (tt, J=12.0, 4.0 Hz, 1H), 4.37 (t, J=5.0 Hz, 2H), 3.8-3.4 (m, 36H), 3.00 (d, J=12.0 Hz, 2H), 2.76-2.60 (m, 2H), 2.52 (td, J=12.0, 1.5 Hz, 2H), 2.19-2.15 (m, 2H), 1.96 (dd, J=15.0, 7.5 Hz, 2H), 1.82 (d, J=13.0 Hz, 2H), 1.46 (q, J=12.0 Hz, 2H), 1.03 (t, J=7.5 Hz, 3H).

Figure 3:
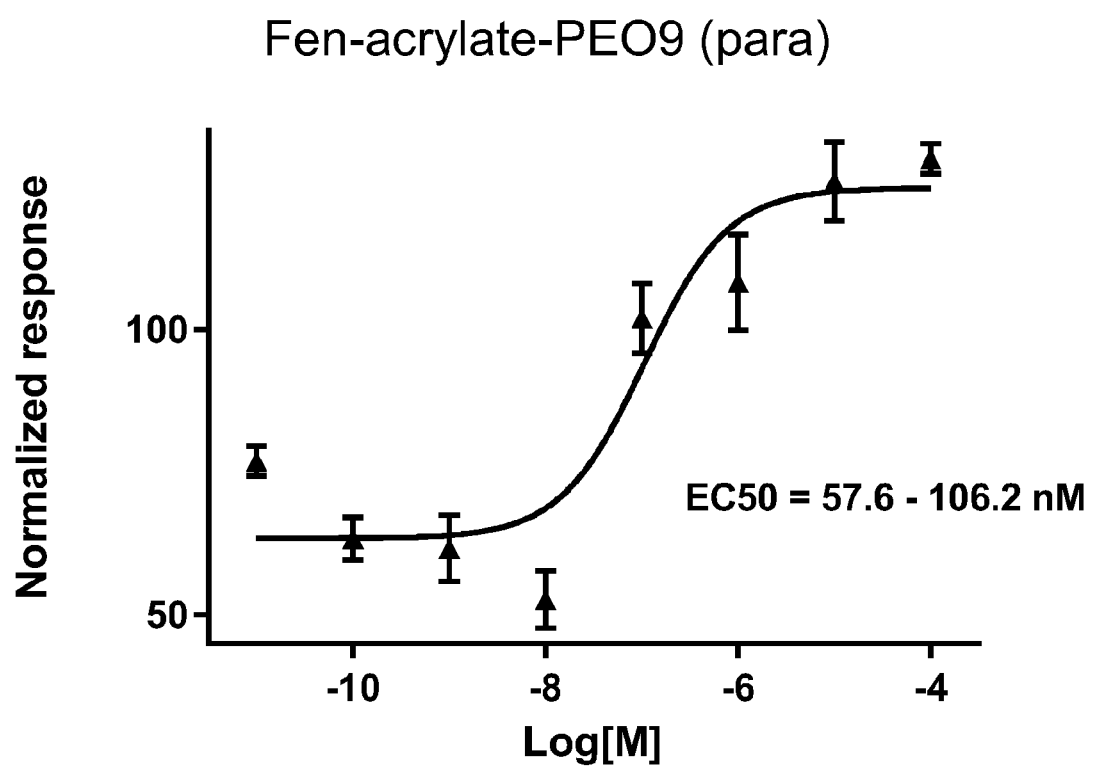
FIG. 3 shows the measurement of Fen-acrylate-PEO9 (para) dose-dependent cAMP inhibition in mu opioid receptor expressing CHO (Chinese hamster ovarian) cells.

FIG. 3 shows the measurement of Fen-acrylate-PEO9 (para) dose-dependent cAMP inhibition in mu opioid receptor expressing CHO (Chinese hamster ovarian) cells.

Example 9

To prepare Fen-Acrylamide-Propyl-OH, Fen-Acry-COOH (160 mg, 0.4 mmol) and 3-amino-1-propanol (60 mg, C0.8 mmol) were dissolved in dichloromethane. EDC (191 mg, 1 mmol) and DMAP (6.1 mg, 0.05 mmol) were added, and the reaction mixture was stirred at room temperature for 24 hours. Additional dichloromethane (50 mL) was added to the reaction mixture, which was then washed with 1 N NaOH, water and brine. The organics was dried over MgSO$_4$, filtered and the solvent was evaporated under vacuum. The crude product was redissolved in ether, and the product was precipitated by dropwise addition of HCl in ethanol. Fen-Acrylamide-Propyl (69%). $^1$H NMR (500 MHz, CDCl$_3$): δ 7.59 (d, J=16.0 Hz, 1H), 7.5-7.4 (m, 5H), 7.26 (d, J=7.0 Hz, 2H), 7.12 (dd, J=8.5, 8.5 Hz, 2H), 6.43 (d, J=16.0 Hz, 1H), 4.81 (tt, J=12.0, 4.0 Hz, 1H), 3.65 (d, J=12.0 Hz, 2H), 3.56 (m, 4H), 3.22 (m, 2H), 3.12 (m, 2H), 2.84 (td, J=12.0, 1.5 Hz, 2H), 2.2-1.9 (m, 6H), 1.76 (m, 2H), 1.04 (t, J=7.5 Hz, 3H).

Figure 7:
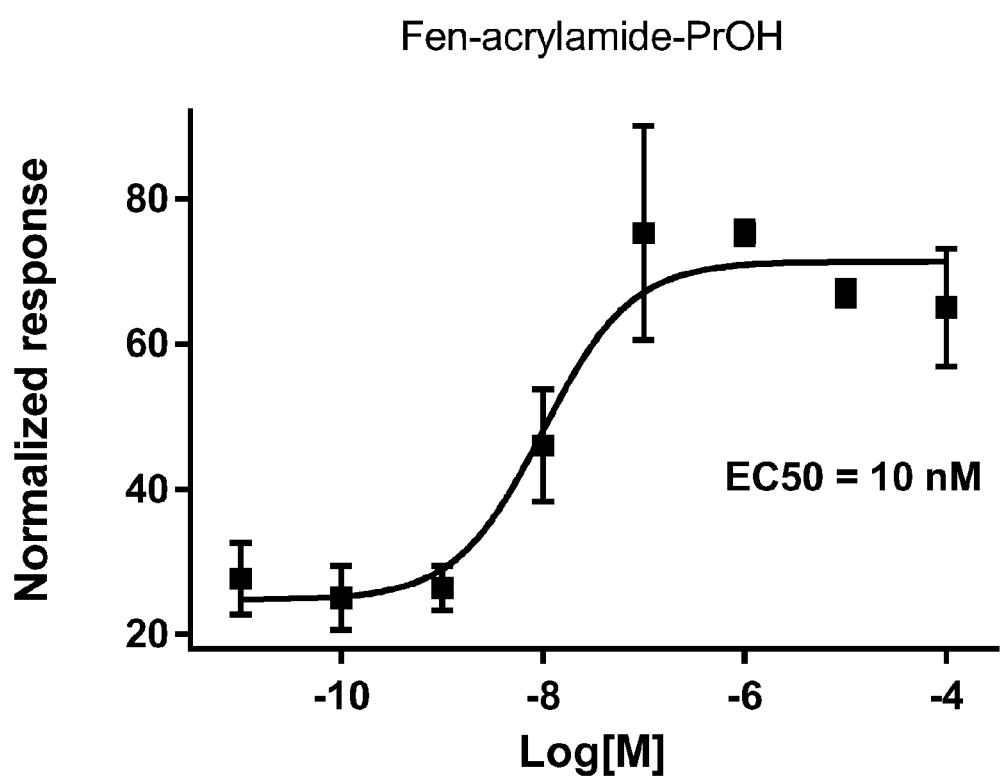
FIG. 7 shows the measurement of Fen-acrylamide-PrOH (propanol) (para) dose-dependent cAMP inhibition in mu opioid receptor expressing CHO (Chinese hamster ovarian) cells.

FIG. 7 shows the measurement of Fen-acrylamide-PrOH (propanol) (para) dose-dependent cAMP inhibition in mu opioid receptor expressing CHO (Chinese hamster ovarian) cells.

Example 10

To prepare Fen-Br Meta, N-phenyl-N-piperidin-4-yl-propionannide (Norfentanyl, 0.93 g, 4.0 mmol) and 3-bromophenethyl bromide (1.58 g, 6.0 mmol) were dissolved in 15 mL DMF, followed by addition of N,N-diisopropylethylamine (0.78 g, 6.0 mmol). The reaction was kept stirring at 60° C. for 24 hours. The reaction mixture was cooled to room temperature before ethyl ether (100 mL) was added, and the organics were washed with 1 N NaOH (30 mL×3), water (30 mL×3) and brine (30 mL×3). The organics were then dried over MgSO$_4$ and concentrated under vacuum. The organics were redissolved in ethyl ether, and pure Fen-Br was precipitated as HCl salt by addition of HCl in ethanol solution. Fen-Br Meta (93%). $^1$H NMR (500 MHz, CDCl$_3$): δ 7.55-7.35 (m, 5H), 7.18 (dd, J=8.5, 8.5 Hz, 2H), 7.09 (d, J=8.5 Hz, 2H), 4.80 (tt, J=12.0, 4.0 Hz, 1H), 3.62 (d, J=12.0 Hz, 2H), 3.12 (m, 2H), 2.89 (td, J=12.0, 1.5 Hz, 2H), 2.2-1.8 (m, 6H), 1.42 (m, 2H), 1.01 (t, J=7.5 Hz, 3H).

Figure 8:
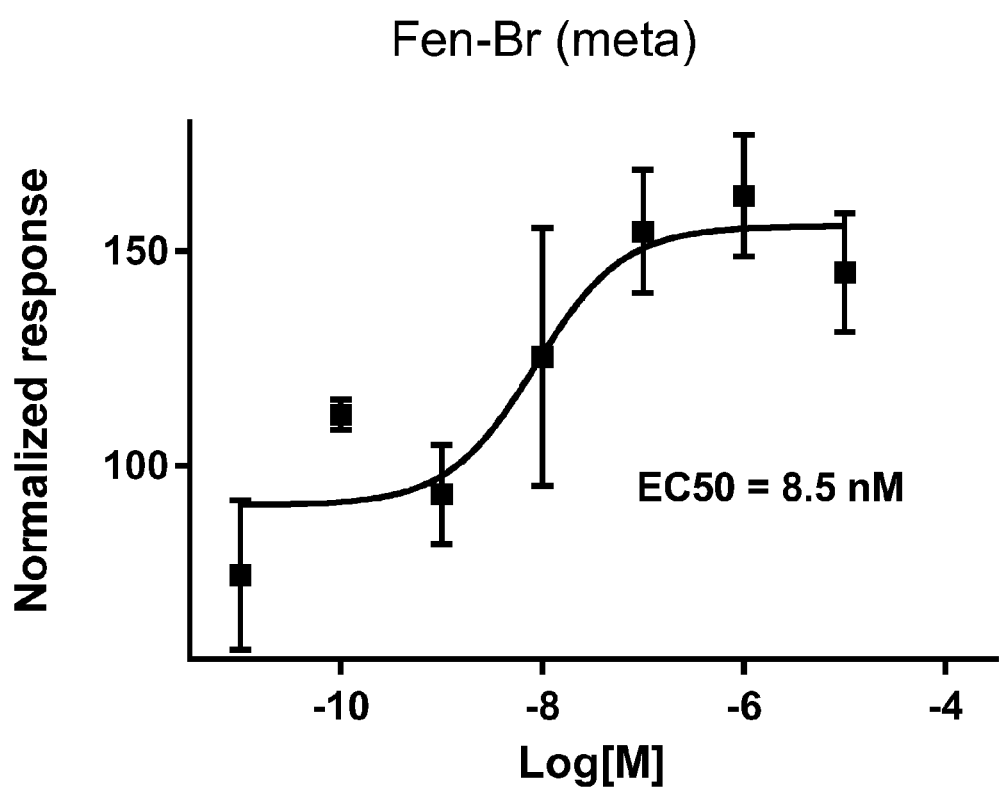
FIG. 8 shows the measurement of Fen-Br (meta) dose-dependent cAMP inhibition in mu opioid receptor expressing CHO (Chinese hamster ovarian) cells.

FIG. 8 illustrates the measurement of Fen-Br (meta) dose-dependent cAMP inhibition in mu opioid receptor expressing CHO (Chinese hamster ovarian) cells

Example 11

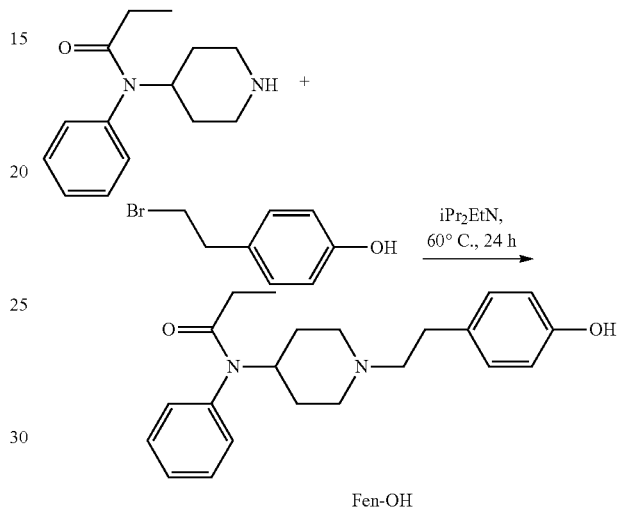

Fen-OH

To prepare Fen-OH, N-phenyl-N-piperidin-4-yl-propionannide (Norfentanyl, 0.93 g, 4.0 mmol) and 4-hydroxyphenethyl bromide (1.21 g, 6.0 mmol) were dissolved in 15 mL DMF, followed by addition of N,N-diisopropylethylamine (0.78 g, 6.0 mmol). The reaction was kept stirring at 60° C. for 24 hours. The reaction mixture was cooled to room temperature before ethyl ether (100 mL) was added, and the organics were washed with 1 N NaOH (30 mL×3), water (30 mL×3) and brine (30 mL×3). The organics were then dried over MgSO$_4$ and concentrated under vacuum. The organics were redissolved in ethyl ether, and pure Fen-OH was precipitated as HCl salt by addition of HCl in ethanol solution (96%). $^1$H NMR (500 MHz, CDCl$_3$): δ 7.45-7.35 (m, 3H), 7.09 (dd, J=8.5, 8.5 Hz, 2H), 6.98 (d, J=8.5 Hz, 2H), 6.76 (d, J=8.5 Hz, 2H), 4.68 (tt, J=12.0, 4.0 Hz, 1H), 2.99 (d, J=12.0 Hz, 2H), 2.67-2.47 (m, 2H), 2.09 (td, J=12.0, 1.5 Hz, 2H), 1.96 (dd, J=15.0, 7.5 Hz, 2H), 1.80 (d, J=13.0 Hz, 2H), 1.44 (q, J=12.0 Hz, 2H), 1.39-1.27 (m, 2H), 1.03 (t, J=7.5 Hz, 3H).

Example 12

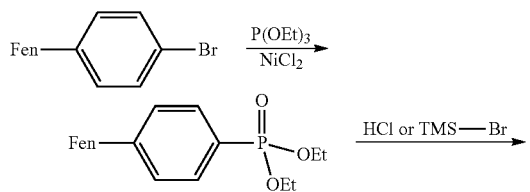

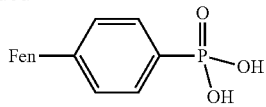

To prepare Fen-PO$_3$Et$_2$, Fen-Br (208 mg, 0.5 mmol) was dissolved in DMF. NiCl$_2$ (6.5 mg, 0.05 mmol) and P(OEt)$_3$ (166 mg, 1 mmol) were added, and the reaction was stirred overnight at 130° C. under N$_2$ protection. The reaction was cooled to room temperature and dissolved in CH$_2$Cl$_2$. The reaction was passed through a short silica gel column to remove the NiCl$_2$ salt. The organics were then washed with water and brine several times, dried over MgSO$_4$ and concentrated in vacuo to afford substantially pure Fen-PO$_3$Et$_2$ (57%). $^1$H NMR (500 MHz, CDCl$_3$): δ 7.5-7.3 (m, 5H), 7.10 (dd, J=8.5, 8.5 Hz, 2H), 7.03 (d, J=8.5 Hz, 2H), 4.70 (tt, J=12.0, 4.0 Hz, 1H), 4.14 (m, 6H), 2.99 (d, J=12.0 Hz, 2H), 2.67-2.47 (m, 2H), 2.09 (td, J=12.0, 1.5 Hz, 2H), 1.96 (dd, J=15.0, 7.5 Hz, 2H), 1.80 (d, J=13.0 Hz, 2H), 1.44 (q, J=12.0 Hz, 2H), 1.39-1.27 (m, 2H), 1.03 (t, J=7.5 Hz, 3H).

To prepare Fen-PO$_3$H$_2$, Fen-PO$_3$Et$_2$ (100 mg, 0.21 mmol) was dissolved in dry CH$_2$Cl$_2$. Trimethylsilyl chloride (54 mg, 0.5 mmol) was added, and the reaction was stirred under N$_2$ for 24 hours. Methanol and water (1:1 v/v, 2 mL) was then added, and the reaction was continued for 24 hours at room temperature. The reaction mixture was placed in vacuo to remove all solvents (90%). $^1$H NMR (500 MHz, CDCl$_3$): δ 7.53-7.47 (m, 5H), 7.14-7.11 (m, 4H), 4.82 (tt, J=12.0, 4.0 Hz, 1H), 3.62 (d, J=12.0 Hz, 2H), 3.21 (m, 2H), 3.09 (td, J=12.0, 1.5 Hz, 2H), 2.81 (dd, J=15.0, 7.5 Hz, 2H), 2.1-1.9 (m, 6H), 1.04 (t, J=7.5 Hz, 3H).

Figure 9:
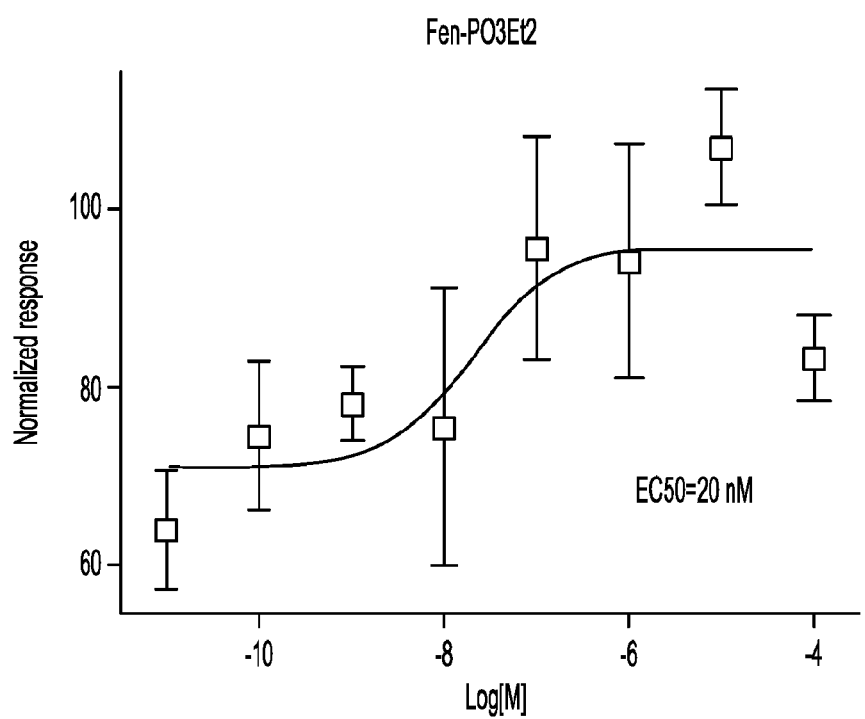
FIG. 9 shows the measurement of Fen-$PO_3Et_2$ (para) dose-dependent cAMP inhibition in mu opioid receptor expressing CHO (Chinese hamster ovarian) cells.

FIG. 9 shows the measurement of Fen-PO$_3$Et$_2$ (para) dose-dependent cAMP inhibition in mu opioid receptor expressing CHO (Chinese hamster ovarian) cells.

Figure 10:
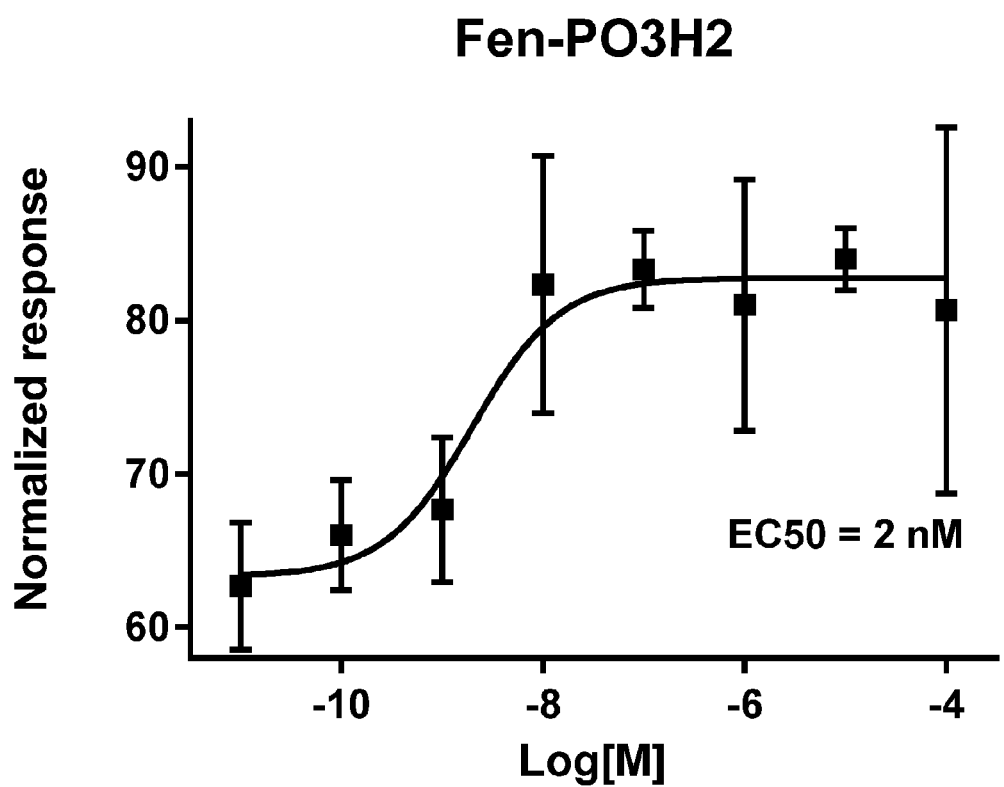
FIG. 10 shows the measurement of Fen-$PO_3OH_2$ (para) dose-dependent cAMP inhibition in mu opioid receptor expressing CHO (Chinese hamster ovarian) cells.

FIG. 10 shows the measurement of Fen-PO$_3$H$_2$ (para) dose-dependent cAMP inhibition in mu opioid receptor expressing CHO (Chinese hamster ovarian) cells.

Example 13

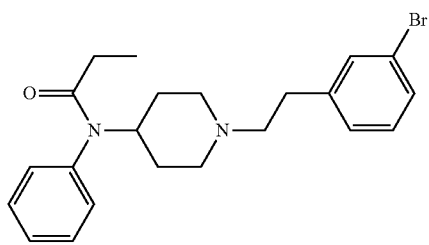

m-Fen-Br

To prepare m-Fen-Br, N-phenyl-N-piperidin-4-yl-propionannide (Norfentanyl, 0.93 g, 4.0 mmol) and 3-bromophenethyl bromide (1.58 g, 6.0 mmol) were dissolved in 15 mL DMF, followed by addition of N,N-diisopropylethylamine (0.78 g, 6.0 mmol). The reaction was kept stirring at 60° C. for 24 hours. The reaction mixture was cooled to room temperature before ethyl ether (100 mL) was added, and the organics were washed with 1 N NaOH (30 mL×3), water (30 mL×3) and brine (30 mL×3). The organics were then dried over MgSO$_4$ and concentrated under vacuum. The organics were redissolved in ethyl ether, and pure m-Fen-Br was precipitated as HCl salt by addition of HCl in ethanol solution. m-Fen-Br (93%). $^1$H NMR (500 MHz, CDCl$_3$): δ 7.55-7.35 (m, 5H), 7.18 (dd, J=8.5, 8.5 Hz, 2H), 7.09 (d, J=8.5 Hz, 2H), 4.80 (tt, J=12.0, 4.0 Hz, 1H), 3.62 (d, J=12.0 Hz, 2H), 3.12 (m, 2H), 2.89 (td, J=12.0, 1.5 Hz, 2H), 2.2-1.8 (m, 6H), 1.42 (m, 2H), 1.01 (t, J=7.5 Hz, 3H).

Example 14

To prepare Fen-N$_3$, CuI (19 mg, 0.1 mmol) and N,N'-Dimethylethylenediamine (16 mg, 0.18 mmol) were dissolved in a mixture of ethanol and water solution (v/v=7:3, 2 mL). The solution was degassed by bubbling with nitrogen for ~30 min, and Fen-Br (415 mg, 1 mmol), sodium azide (0.95 g, 15 mmol), and sodium ascorbate (12 mg, 0.06 mmol) were added. The reaction was kept reflux for 3 hours before was cooled to room temperature. Ether (30 mL) was added to the reaction mixture, and the organics were washed with 1 N NaOH (10 mL×3), water (10 mL×3) and brine (10 mL×3). The organics were then dried over MgSO$_4$ and evaporated under vacuum to afford substantially pure Fen-N$_3$ (81%). $^1$H NMR (500 MHz, CDCl$_3$): δ 7.43-7.37 (m, 3H), 7.15 (dd, J=8.5, 8.5 Hz, 2H), 7.10 (d, J=7.0 Hz, 2H), 6.94 (d, J=8.5 Hz, 2H), 4.70 (tt, J=12.0, 4.0 Hz, 1H), 3.00 (d, J=12.0 Hz, 2H), 2.76-2.60 (m, 2H), 2.52 (td, J=12.0, 1.5 Hz, 2H), 2.19-2.15 (m, 2H), 1.96 (dd, J=15.0, 7.5 Hz, 2H), 1.82 (d, J=13.0 Hz, 2H), 1.46 (q, J=12.0 Hz, 2H), 1.03 (t, J=7.5 Hz, 3H).

Example 15

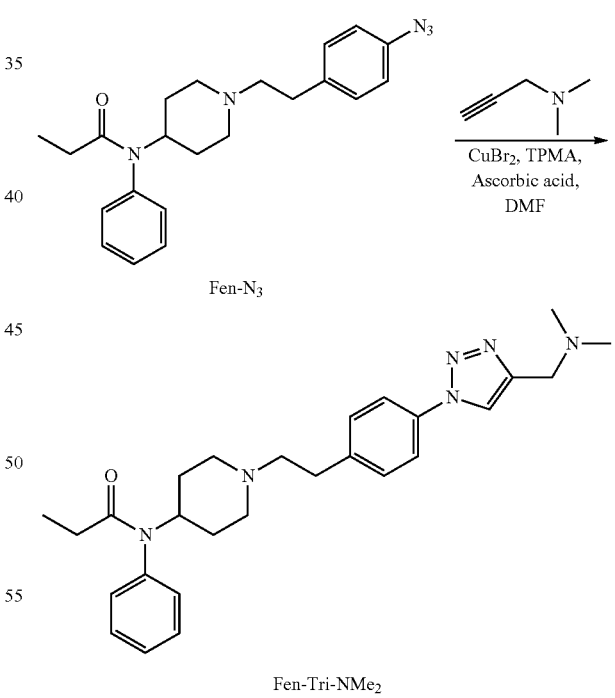

To prepare Fen-Tri-NMe$_2$, CuBr$_2$ (13.5 mg, 0.06 mmol) and TPMA (17.4 mg, 0.06 mmol) were mixed and dissolved in 2 mL DMF. Fen-N$_3$ (200 mg, 0.53 mmol) and 3-dimethylamino-1-propyne (208 mg, 2.5 mmol) were added, and the reaction mixture was degassed by bubbling with N$_2$ gas for 30 min. A deoxygenated ascorbic acid solution (21.0 mg in 0.5 mL DMF) was injected to the reaction container, and the reaction was stirred at room temperature for 24 hours. The reaction mixture was passed through a neutral Al₂O₃ column to remove the copper catalyst, and was added to 1 M NaOH to allow for precipitation of the crude product. The precipitate was washed with water, dried, dissolved in ethyl ether and was reprecipitated by addition of HCl in ethanol. Recrystallization by methanol/ethyl ether afforded pure product. Fen-Tri-NMe₂ (78%). ¹H NMR (500 MHz, CDCl₃): δ 7.90 (s, 1H), 7.62 (d, J=8.5 Hz, 2H), 7.44-7.37 (m, 3H), 7.31 (d, J=8.5 Hz, 2H), 7.10 (d, J=7.0 Hz, 2H), 4.71 (tt, J=12.0, 4.0 Hz, 1H), 3.70 (s, 2H), 3.00 (d. J=12.0 Hz, 2H), 2.76-2.60 (m, 2H), 2.52 (td, J=12.0, 1.5 Hz, 2H), 2.35 (s, 6H), 2.19-2.15 (m, 2H), 1.96 (dd, J=15.0, 7.5 Hz, 2H), 1.82 (d, J=13.0 Hz, 2H), 1.46 (q, J=12.0 Hz, 2H), 1.03 (t, J=7.5 Hz, 3H).

Example 16

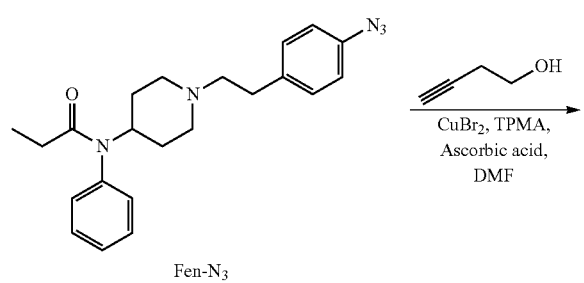

Fen-N₃

CuBr₂, TPMA, Ascorbic acid, DMF

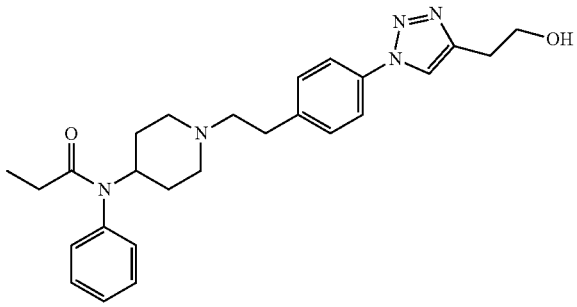

Fen-Tri-EtOH

To prepare Fen-Tri-EtOH, the procedure was the same as for Example 14, except 3-Butyn-1-ol (175 mg, 2.5 mmol) was added in place of the 3-dimethylamino-1-propyne. Fen-Tri-EtOH (84%). ¹H NMR (500 MHz, CDCl₃): δ 7.81 (s, 1H), 7.62 (d, J=8.5 Hz, 2H), 7.44-7.37 (m, 3H), 7.31 (d, J=8.5 Hz, 2H), 7.10 (d, J=7.0 Hz, 2H), 4.71 (tt, J=12.0, 4.0 Hz, 1H), 4.03 (t, J=6.0, 2H), 3.05 (t, J=6.0, 2H), 3.00 (d, J=12.0 Hz, 2H), 2.76-2.60 (m, 2H), 2.52 (td, J=12.0, 1.5 Hz, 2H), 2.19-2.15 (m, 2H), 1.96 (dd, J=15.0, 7.5 Hz, 2H), 1.82 (d, J=13.0 Hz, 2H), 1.46 (q, J=12.0 Hz, 2H), 1.03 (t, J=7.5 Hz, 3H).

Examples 17-21

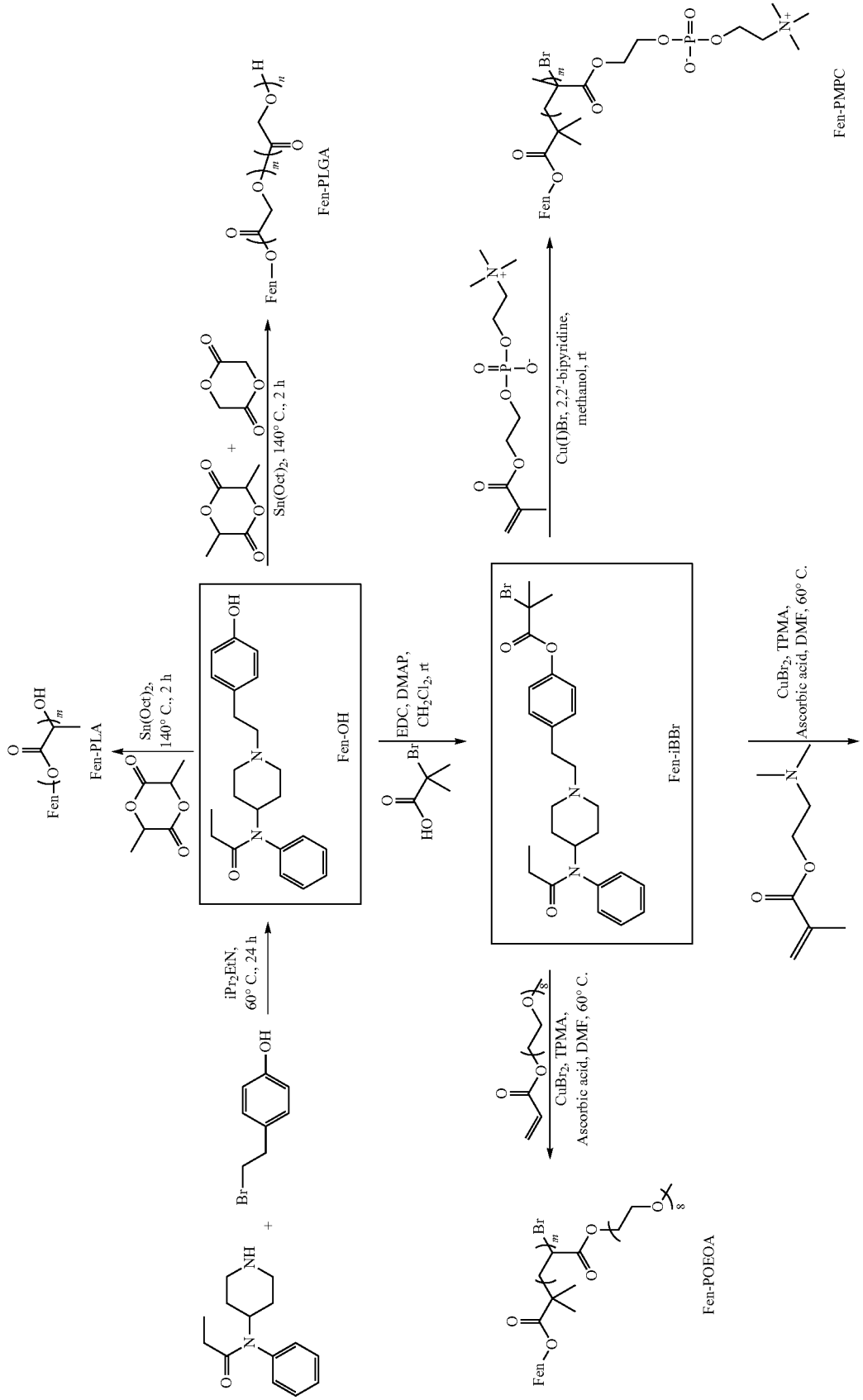

-continued
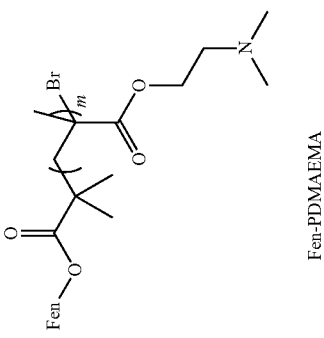
Fen-PDMAEMA
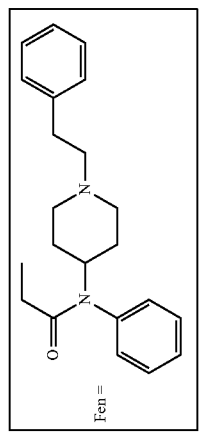
Fen =

Example 17

To prepare Fen-PLA, Fen-OH (100 mg, 0.28 mmol), lactide (1.0 g, 6.9 mmol), and stannous octoate (20 mg, 49 µmol) were added to a schlenk flask equipped with a magnetic stir bar and a rubber septum. The flask was air-tightly sealed and was purged with dry $N_2$ gas for 1 hour. The reaction mixture was then heated at 140° C. and stirred for 2 h. The reaction was cooled to room temperature, and dichloromethane (10 mL) was added to dissolve the product. The polymer was purified by precipitation from mixture of methanol and water. Fen-PLA (90%). $^1$H NMR (500 MHz, $CDCl_3$): δ 5.3-5.1 (br), 4.39 (s), 1.6-1.4 (br). SEC: $M_n$=9500, $M_w/M_n$=1.35.

Figure 11:
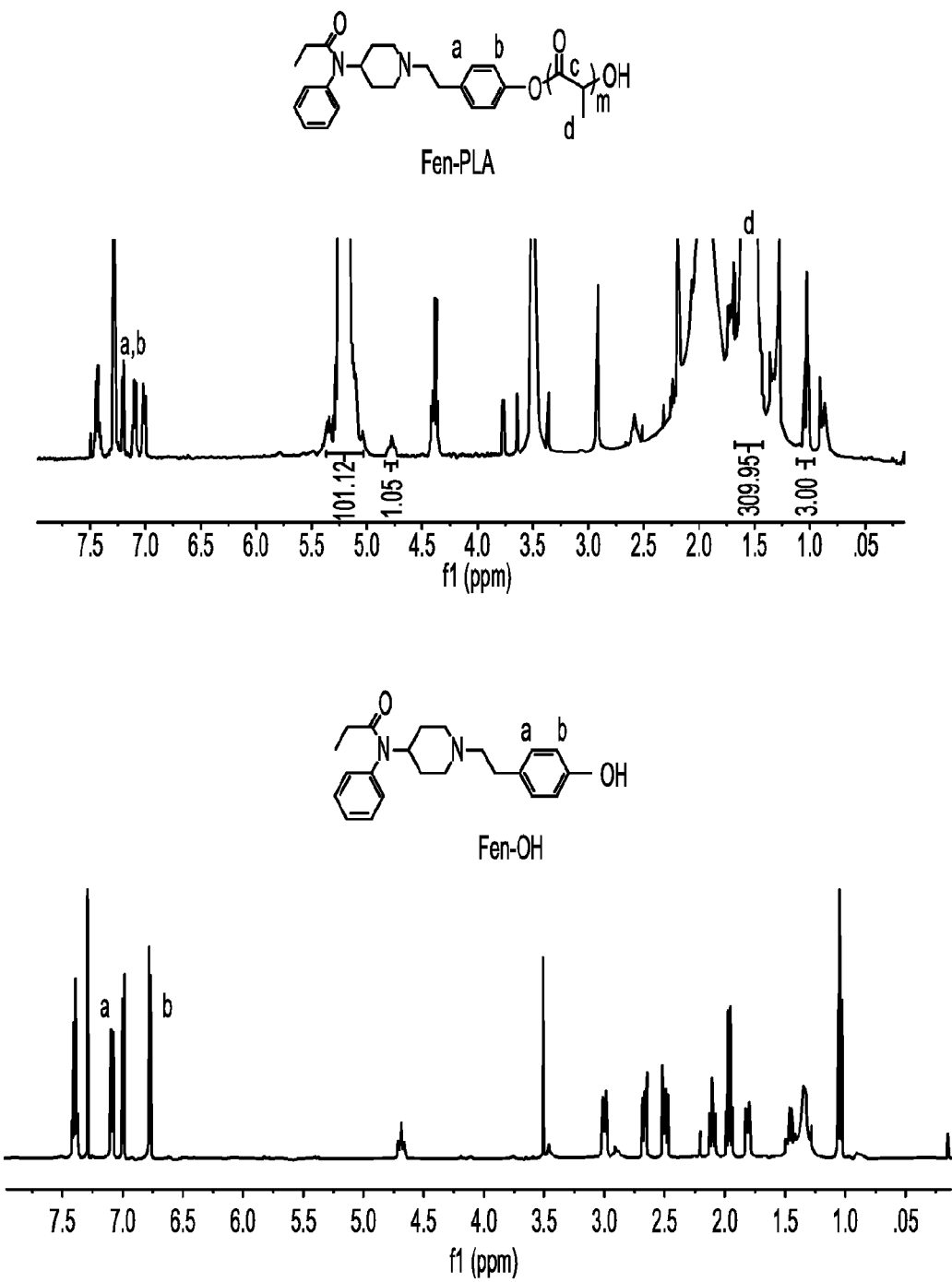
FIG. 11 is the $^1$H NMR (nuclear magnetic resonance) spectra of Fentanyl-OH (para) and Fentanyl-O-Poly(lactic acid).

FIG. 11 is the $^1$H NMR (nuclear magnetic resonance) spectra of Fentanyl-OH (para) and Fentanyl-O-Poly(lactic acid).

Figure 12:
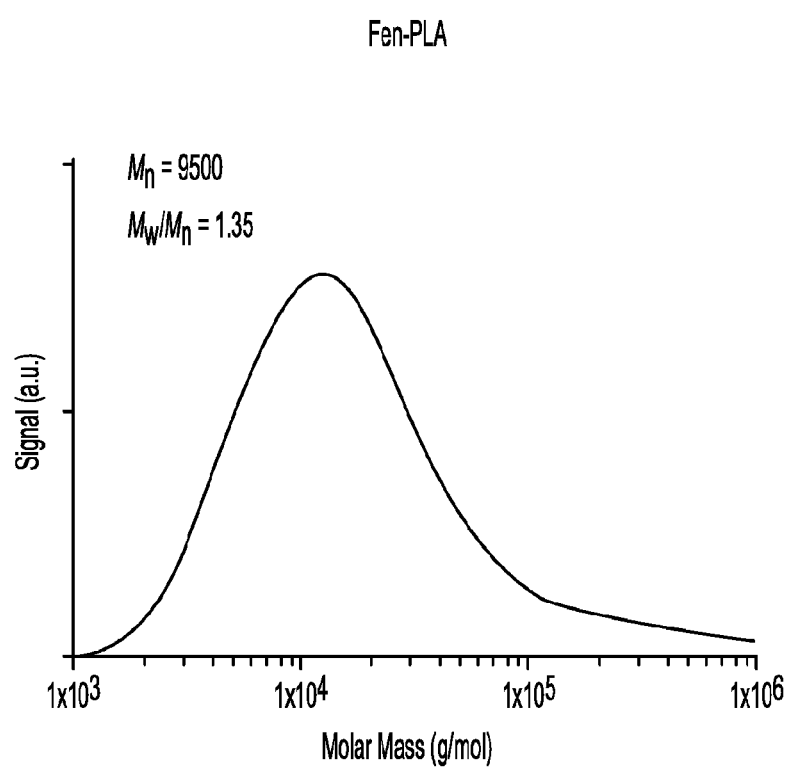
FIG. 12 is the gel permeation chromatography trace of Fentanyl-O-Poly(lactic acid).

FIG. 12 is the gel permeation chromatography trace of Fentanyl-O-Poly(lactic acid).

Example 18

To prepare Fen-PLGA, Fen-OH (150 mg, 0.28 mmol), lactide (1.0 g, 6.9 mmol), glycolide (1.0 g, 8.6 mmol), and stannous octoate (40 mg, 98 µmol) were added to a schlenk flask equipped with a magnetic stir bar and a rubber septum. The flask was air-tightly sealed and was purged with dry $N_2$ gas for 1 hour. The reaction mixture was then heated at 180° C. and stirred for 2 h. The reaction was cooled to room temperature and dichloromethane (10 mL) was added to dissolve the product. The solution was filtered and was dialyzed against methanol and acetone. Fen-PLGA (85%). $^1$H NMR (500 MHz, $CDCl_3$): δ 5.3-5.1 (br), 5.0-4.6 (br), 1.6-1.4 (br). SEC: M=14000, $M_w/M_n$=2.45.

Figure 13:
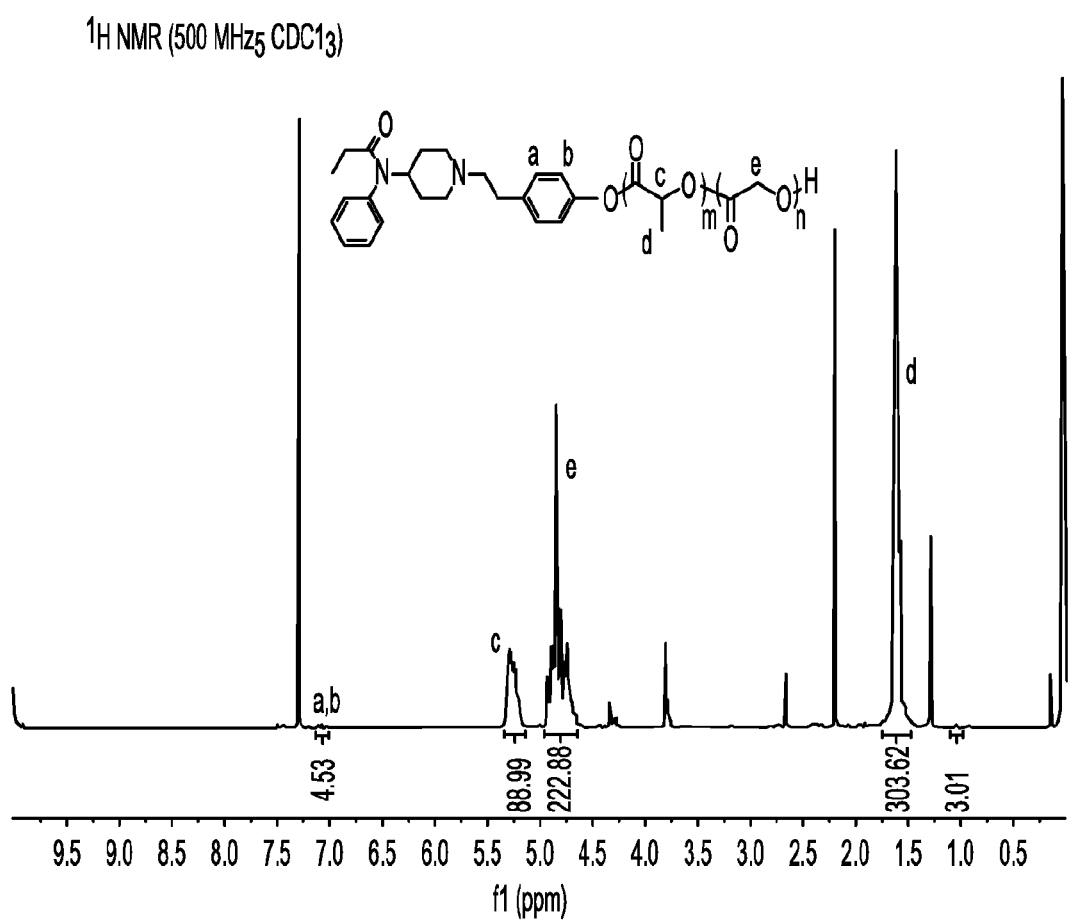
FIG. 13 is the $^1$H NMR (nuclear magnetic resonance) spectra of Fentanyl-O-Poly(lactic acid-co-glycolic acid).

FIG. 13 is the $^1$H NMR (nuclear magnetic resonance) spectra of Fentanyl-O-Poly(lactic acid-co-glycolic acid).

Figure 14:
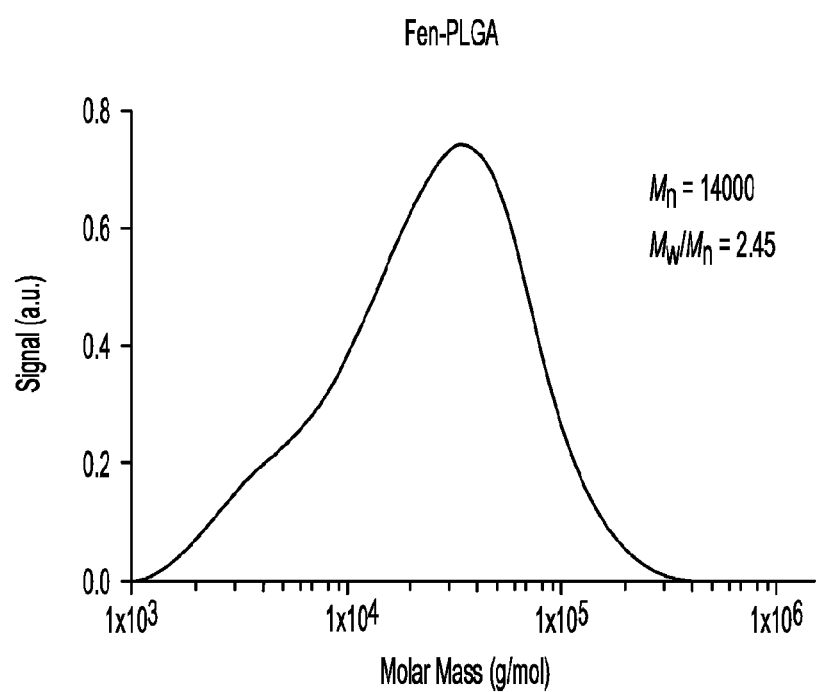
FIG. 14 is the gel permeation chromatography trace of Fentanyl-O-Poly(lactic acid-co-glycolic acid).

FIG. 14 is the gel permeation chromatography trace of Fentanyl-O-Poly(lactic acid-co-glycolic acid).

Example 19

To prepare Fen-iBBr, Fen-OH (100 mg, 0.28 mmol) and 2-Bromo-2-methylpropionic acid (66.8 mg, 0.4 mmol) were dissolved in $CH_2Cl_2$ (5 mL). EDC.HCl (95.9 mg, 0.5 mmol) and DMAP (3.0 mg, 0.025 mmol) were added slowly, and the reaction mixture was stirred at room temperature overnight. Addition dichloromethane (15 mL) was added, and the reaction mixture was washed with 1 M HCl (10 mL×3), 1 M NaOH (10 mL×3), and brine (10 mL×3). The organic phase was dried over $MgSO_4$ and was removed under vacuum. Fen-iBBr (85%). $^1$H NMR (500 MHz, $CDCl_3$): δ 7.45-7.35 (m, 3H), 7.20 (d, J=8.5 Hz, 2H), 7.08 (dd, J=8.5, 8.5 Hz, 2H), 7.01 (d, J=8.5 Hz, 2H), 4.71 (tt, J=12.0, 4.0 Hz, 1H), 3.04 (d, J=12.0 Hz, 2H), 2.77 (m, 2H), 2.57 (m, 2H), 2.22 (m, 2H), 2.06 (s, 6H), 1.93 (d, J=13.0 Hz, 2H), 1.82 (q, J=12.0 Hz, 2H), 1.50 (m, 2H), 1.03 (t, J=7.5 Hz, 3H).

Example 20

To prepare Fen-POEOA, $CuBr_2$ (0.8 mg, 3.6 µmol) and TPMA (3.1 mg, 10.8 µmol) were added to a Schlenk flask and dissolved in 1 mL DMF. $OEOA_{480}$ (1.92 g, 4 mmol) and Fen-iBBr (20.0 mg, 0.04 mmol) were added, and the flask was tightly sealed with rubber septum. The reaction mixture was then degassed by purging with $N_2$ gas for 30 minutes. The flask was then heated to 40° C., and a deoxygenated ascorbic acid solution (100 µL, 360 mM in DMF) was quickly injected into the reaction mixture via a syringe under $N_2$ protection. The polymerization was continued for 180 min before was stopped. The crude polymer was purified by repeated precipitation from ethyl ether. SEC: $M_n$=7100 g $mol^{-1}$, $M_w/M_n$=1.41. $^1$H NMR (500 MHz, $CDCl_3$): δ=4.17, 3.8-3.5, 3.39, 2.4-1.2, 1.99, 1.61.

Figure 15:
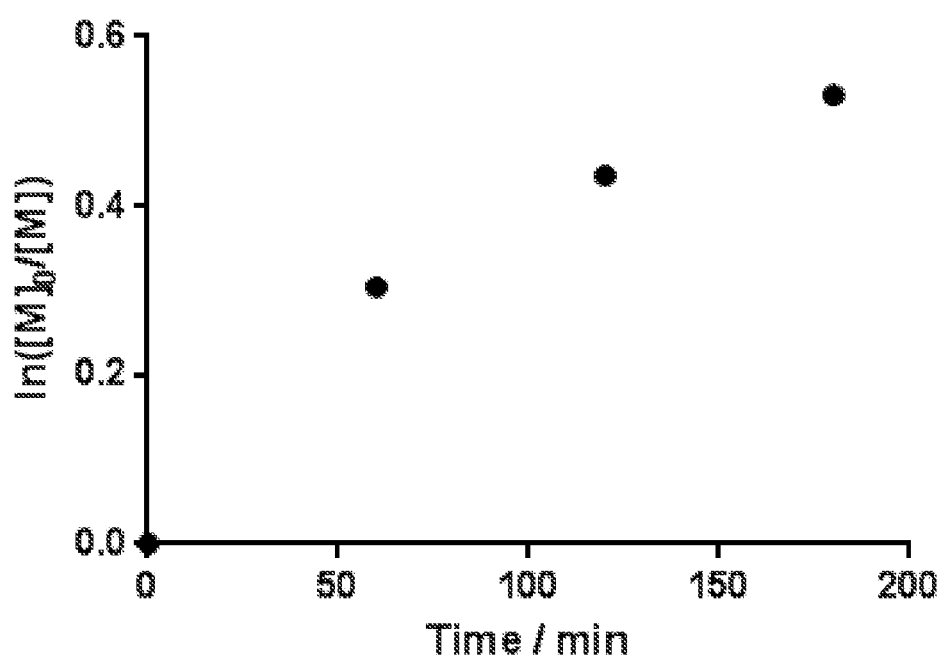
FIG. 15 is the semi-logarithmic plot of oligoethyleneoxide acrylate monomer conversion into polymer grown from Fen-O-iBBr (ATRP initiator).

FIG. 15 is the semilogarithmic plot of oligoethyleneoxide acrylate monomer conversion into polymer grown from Fen-O-iBBr (ATRP initiator).

Figure 16:
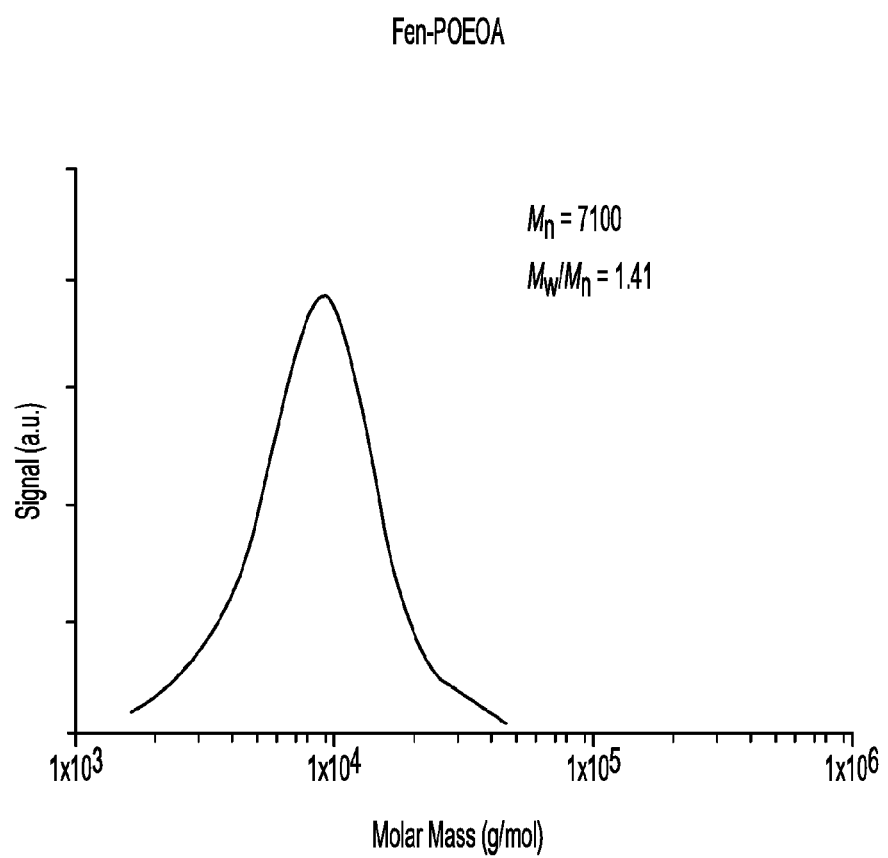
FIG. 16 is the gel permeation chromatography trace of Fentanyl-O-Poly(oligoethyleneoxide acrylate).

FIG. 16 is the gel permeation chromatography trace of Fentanyl-O-Poly(oligoethyleneoxide acrylate)

Example 21

To prepare Fen-PDMAEMA, $CuBr_2$ (0.8 mg, 3.6 µmol) and TPMA (3.1 mg, 10.8 µmol) were added to a Schlenk flask and dissolved in 1 mL DMF. 2-(Dimethylamino)ethyl methacrylate (628 mg, 4 mmol) and Fen-iBBr (20.0 mg, 0.04 mmol) were added, and the flask was tightly sealed with rubber septum. The reaction mixture was then degassed by purging with $N_2$ gas for 30 minutes. The flask was then heated to 40° C., and a deoxygenated ascorbic acid solution (100 µL, 360 mM in DMF) was quickly injected into the reaction mixture via a syringe under $N_2$ protection. The polymerization was continued for 35 min before was stopped. The crude polymer was purified by repeated precipitation from ethyl ether. SEC: $M_n$=2600 g $mol^{-1}$, $M_w/M_n$=1.48. $^1$H NMR (500 MHz, $CDCl_3$): δ=4.62, 4.08, 3.7-3.3, 2.60, 2.31, 2.0-1.7, 1.08, 0.91.

Figure 17:
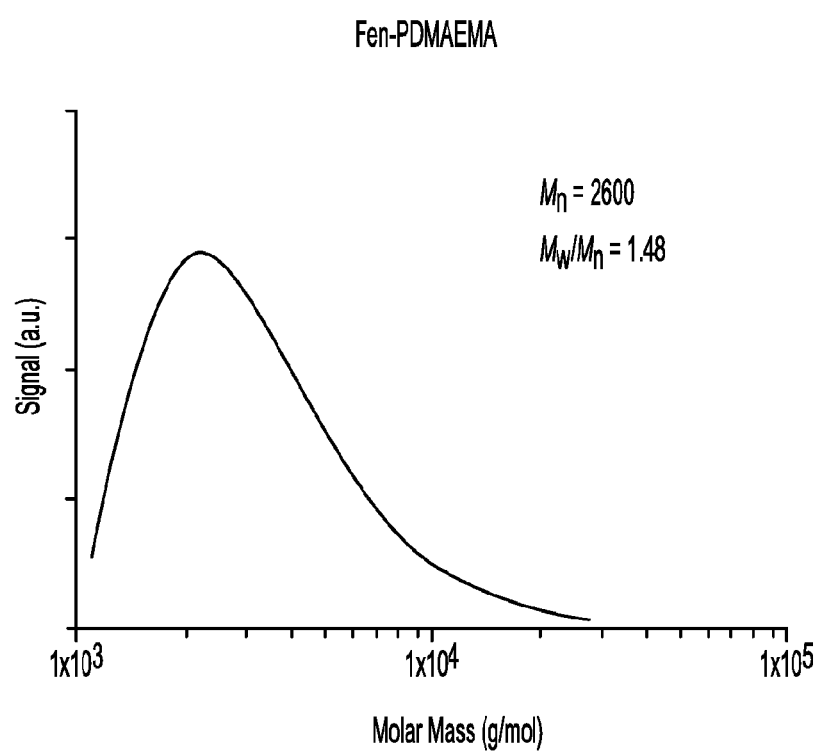
FIG. 17 is the gel permeation chromatography trace of Fentanyl-O-Poly(dimethylethyl acrylate).

FIG. 17 is the gel permeation chromatography trace of Fentanyl-O-Poly(dimethylethyl acrylate).

Examples 22-25

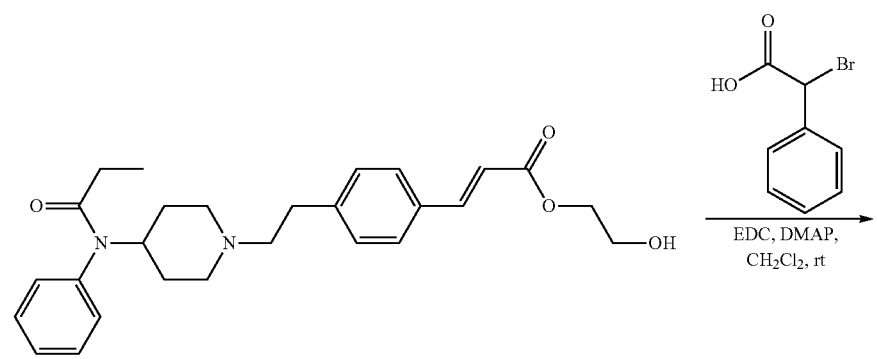

37 38

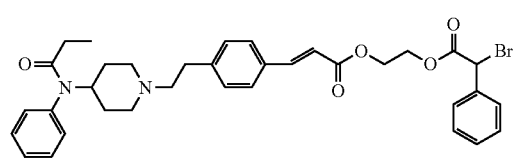

Fen-Acry-EtBPA

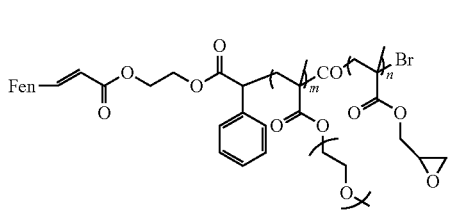

Fen-Acry-P(OEOMA-co-GMA)

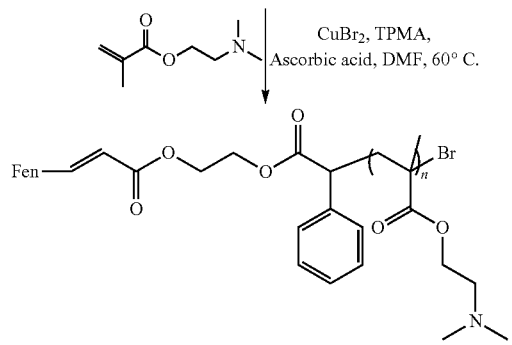

Fen-Acyl-PDMAEMA

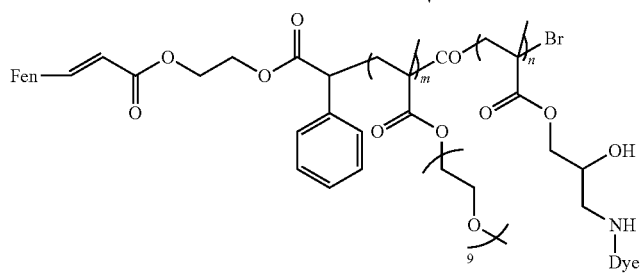

Fen-Acry-P(OEOMA-co-GMA)Dye

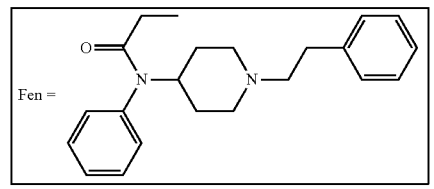

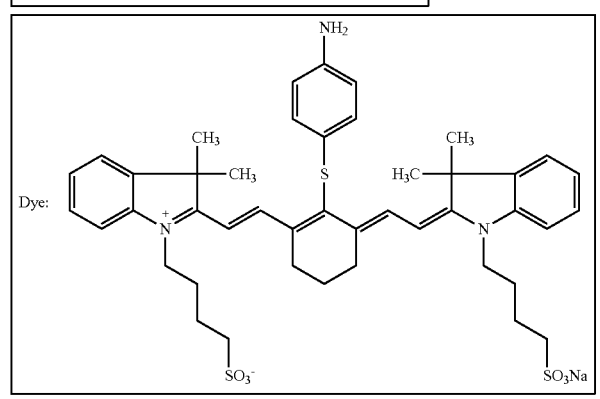

Example 22

To prepare Fen-Acry-EtBPA, Fen-Acry-EtOH (200 mg, 0.4 mmol) and α-bromophenylacetic acid (108 mg, 0.5 mmol) were dissolved in $CH_2Cl_2$ (5 mL). EDC. HCl (95.9 mg, 0.5 mmol) and DMAP (3.0 mg, 0.025 mmol) were added slowly, and the reaction mixture was stirred at room temperature overnight. Additional dichloromethane (15 mL) was added, and the reaction mixture was washed with 1 M NaOH, water and brine. The organic phase was dried over $MgSO_4$ and was removed under vacuum. The crude product was further purified by column chromatography (ethyl acetate/methanol=5:1) to afford pure product (77%). $^1$H NMR (500 MHz, $CDCl_3$): δ 7.60 (d, J=16.0 Hz, 1H), 7.45-7.39 (m, 5H), 7.22 (d, J=7.0 Hz, 2H), 7.09 (dd, J=8.5, 8.5 Hz, 2H), 6.30 (d, J=16.0 Hz, 1H), 5.40 (s, 1H), 4.70 (tt, J=12.0, 4.0 Hz, 1H), 4.45 (t, J=5.0 Hz, 2H), 4.36 (t, J=5.0 Hz, 2H), 3.01 (d, J=12.0 Hz, 2H), 2.78 (m, 2H), 2.54 (m, 2H), 2.15 (td, J=12.0, 1.5 Hz, 2H), 2.0-1.5 (m, 6H), 1.02 (t, J=7.5 Hz, 3H).

Example 23

To prepare Fen-Acry-P(OEOMA-co-GMA), $CuBr_2$ (0.8 mg, 3.6 μmol) and TPMA (3.1 mg, 10.8 μmol) were added to a Schlenk flask and dissolved in 0.5 mL DMF. $OEOMA_{500}$ (1.8 g, 3.6 mmol), GMA (56.8 mg, 0.4 mmol), and Fen-Acry-EtBPA (22.0 mg, 0.04 mmol) were added, and the flask was tightly sealed with rubber septum. The reaction mixture was then degassed by purging with $N_2$ gas for 30 minutes. The flask was then heated to 40° C., and a deoxygenated ascorbic acid solution (100 μL, 36 mM in DMF) was quickly injected into the reaction mixture via a syringe under $N_2$ protection. The polymerization was continued for 60 min before was stopped. The crude polymer was purified by repeated precipitation from ethyl ether. $^1$H NMR (500 MHz, CDCl$_3$): δ=4.30, 4.10, 3.88, 3.8-3.5, 3.40, 3.20, 2.85, 2.67, 2.2-1.5, 1.03, 0.87.

Example 24

To prepare Fen-Acry-P(OEOMA-co-GMA)-dye, Fen-Acry-P(OEOMA-co-GMA) (100 mg) and ADS790WS dye (8 mg, 0.01 mmol) were dissolved together in trifluoroethanol (2 mL). The reaction mixture was kept stirring at 50° C. for 48 hours. The polymer was purified by dialysis against water and methanol and dried under high vacuum.

Example 25

To prepare Fen-Acry-PDMAEMA, CuBr$_2$ (0.8 mg, 3.6 μmol) and TPMA (3.1 mg, 10.8 μmol) were added to a Schlenk flask and dissolved in 1 mL DMF. 2-(Dimethylamino)ethyl methacrylate (628 mg, 4 mmol) and Fen-Acry-EtBPA (22.0 mg, 0.04 mmol) were added, and the flask was tightly sealed with rubber septum. The reaction mixture was then degassed by purging with N$_2$ gas for 30 minutes. The flask was then heated to 40° C., and a deoxygenated ascorbic acid solution (100 μL, 36 mM in DMF) was quickly injected into the reaction mixture via a syringe under N$_2$ protection. The polymerization was continued for 90 minutes before was stopped. The crude polymer was purified by repeated precipitation from ethyl ether. $^1$H NMR (500 MHz, CDCl$_3$): δ=4.62, 4.07, 2.57, 2.29, 2.0-1.7, 1.06, 0.91.

Example 26

Norfentanyl (0.93 g, 4.0 mmol) and N,N-diisopropylethylamine (0.78 g, 6.0 mmol) were dissolved in 15 mL DMF and 15 mL CH$_2$Cl$_2$. The reaction container was cooled to 0° C. with an ice bath, and alkyne-alkyle halide (6.0 mmol) was added dropwise. The reaction was kept stirring at 0° C. for 1 hour then at room temperature for 24 hours. Ether (100 mL) was added to the reaction mixture, and the organics were washed with 1 N NaOH (30 mL×3), water (30 mL×3) and brine (30 mL×3). The organics were then dried over MgSO$_4$. HCl in ethanol was added slowly and the precipitate was collected by filtration and dried under vacuum.

Example 27

Norfentanyl (0.93 g, 4.0 mmol) and N,N-diisopropylethylamine (0.78 g, 6.0 mmol) was dissolved in 15 mL DMF and 15 mL CH$_2$Cl$_2$. The reaction container was cooled to 0° C. with an ice bath, and propargyl bromide (0.71 g, 6.0 mmol) was added dropwise. The reaction was kept stirring at 0° C. for 1 hour then at room temperature for 24 hours. Ether (100 mL) was added to the reaction mixture, and the organics were washed with 1 N NaOH (30 mL×3), water (30 mL×3) and brine (30 mL×3). The organics were then dried over MgSO$_4$. HCl in ethanol was added slowly and the precipitate was collected by filtration and dried under vacuum.

Example 28

Norfen-alkyne (270 mg 0.1 mmol) and 2-(2-(2-azidoethoxy)ethox)ethanol (525 mg 3 mmol) were dissolved in 2 ml of DMF. CuBr$_2$ (2.7 mg 0.012 mmol) and TPMA (6.4 mg 0.02 mmol) were added to the reaction mixture followed by ascorbic acid (42 mg, 0.23 mmol) the reaction was stirred for 16 hours at 25° C. The reaction mixture was diluted with 20 mL of dichloromethane and passed over an aluminum oxide column to remove the copper catalyst. The reaction mixture was then washed with 1N NaOH three times, water and brine. The organics were then dried over MgSO$_4$. HCl in ethanol was added slowly and the precipitate was collected by filtration and dried under vacuum.

Example 29

The in vivo antinociceptive properties of various compounds of this disclosure were evaluated using a hot plate withdrawal assay. Male CD-1 mice weighing 30 g (n=10) were dosed subcutaneously 30 min prior to placement on a 55° C. hot plate, and withdrawal latencies were measured (jumping or hind-paw licking) within a 30 second time frame. The mean protective effects at a 95% confidence interval were calculated according to the following equation MPE=100*(Time$_{Latency}$-Time$_{Saline}$)/(30 seconds-Time$_{Saline}$).

The MPE for the hydrophobic compounds Fen-Br and Fen-Acryl-butyl were 73% at 2.4 mg/kg and 94% at 0.54 mg/kg respectively compared to an MPE of 65% at 0.06 mg/kg. The Fen-Acrylate-PEO$_9$ had a MPE of 87% at 12.7 mg/kg. These results indicate that acrylate linking group can be used to prepare compounds with good in vivo activity. The high dose required for the Fen-Acrylate-PEO$_9$ can be explained by the relatively poorer permeability of these compounds as well as being restricted to peripheral mu opioid receptors preventing neural mu opioid receptor binding.

Example 30

To test certain fentanyl derivatives described in this document, CHO cells expressing the human μ-opioid receptor (referred to in this document as CHO-MORs) were cultured at 37° C., at 5% CO$_2$ in a humid cell culture chamber in suitable cell culture media (Hams F12 from Invitrogen with 10% fetal bovine serum). Cells were plated at 90% confluency in white 96 well plates. Prior to the cAMP assay, induction buffer (1x PBS, 500 μM IBMX, 100 μM Ro-20-1724) was added to each well, and incubated at 37° C. for 30 minutes. Cells were incubated for additional 30 minutes with the Opioid-derivative at a range of concentrations (10-11-10-4) with 25 μM Forskolin. Cyclic adenosine monophosphate (cAMP) levels were determined using a cAMP-Glo kit from Promega using the manufacturer's instructions. The synthetic opioid DAMGO was used as positive control. EC$_{50}$ values were determined were determined from the dose response curve using GraphPad. Results are shown in Table 1 below:

TABLE 1

| Name | Structure | predicted PSA | PSA/PSA-fentanyl | log P | MW | MW/Fentanyl | EC50 (nM) |
|---|---|---|---|---|---|---|---|
| Fentanyl | 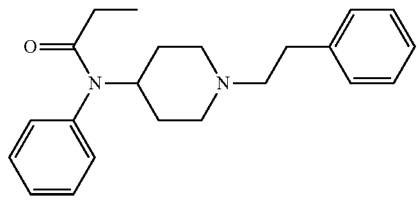 [SMILES: CCC(=O)N(c1ccccc1)C1CCN(CCc2ccccc2)CC1] | 23.55 | 1.00 | 3.8 | 336.47 | 1.0 | 1.7 |
| m-Fen-Br | 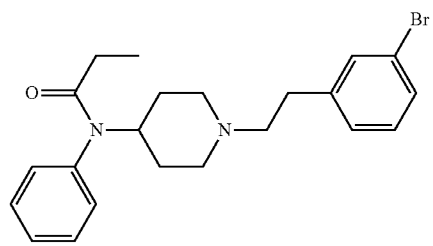 [SMILES: CCC(=O)N(c1ccccc1)C1CCN(CCc2cccc(Br)c2)CC1] | 23.55 | 1.00 | 4.6 | 415.37 | 1.2 | 8.5 |
| p-Fen-Br | 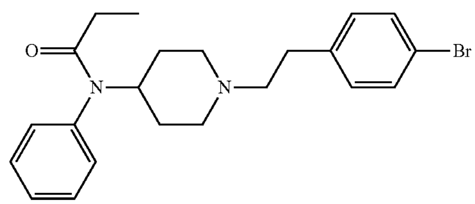 [SMILES: CCC(=O)N(c1ccccc1)C1CCN(CCc2ccc(Br)cc2)CC1] | 23.55 | 1.00 | 4.6 | 415.37 | 1.2 | 6.5 |
| Fen-Azide | 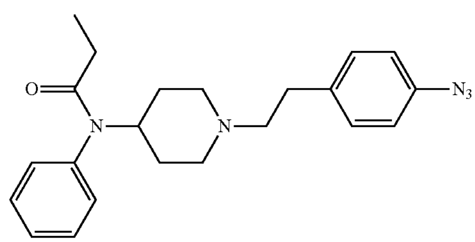 [SMILES: CCC(=O)N(c1ccccc1)C1CCN(CCc2ccc(N=[N+]=[N-])cc2)CC1] | 72.31 | 3.07 | 4.06 | 377.49 | 1.1 | n/a |
| Fen-Acr-PEO9 | 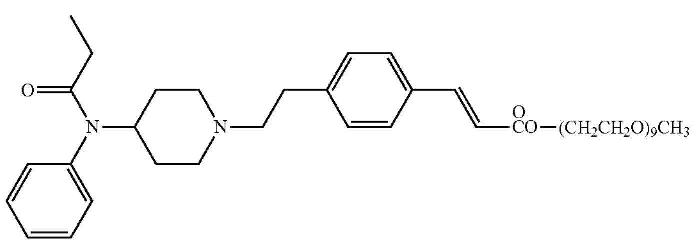 | 132.96 | 5065 | 2.55 | 817.03 | 2.4 | 17 |
| Fen-Acr-Bu | 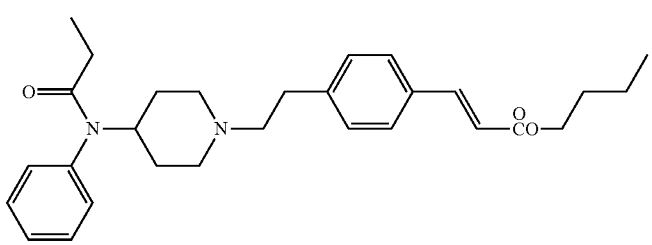 | 49.85 | 2.12 | 5.55 | 462.63 | 1.4 | 9 |

TABLE 1-continued

| Name | Structure | predicted PSA | PSA/ PSA-fentanyl | log P | MW | MW/ Fentanyl | EC50 (nM) |
|---|---|---|---|---|---|---|---|
| Fen-Acr-tBu | 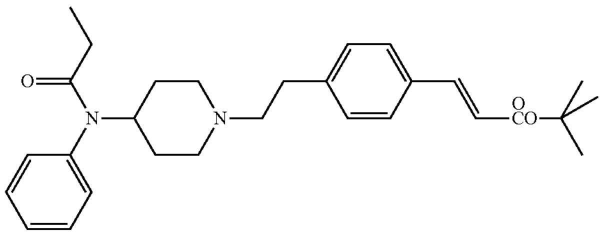 | 49.85 | 2.12 | 5.03 | 462.63 | 1.4 | 69 |
| Fen-SO2N-ME2 | 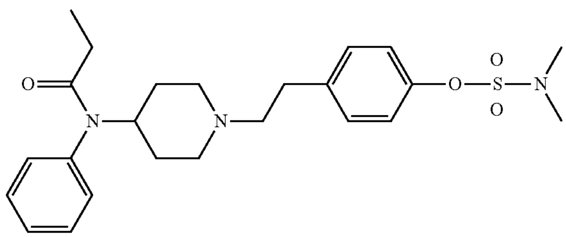 | 70.16 | 2.98 | 3.23 | 459.61 | 1.4 | 26 |
| Fen-Tri-NMe2 | 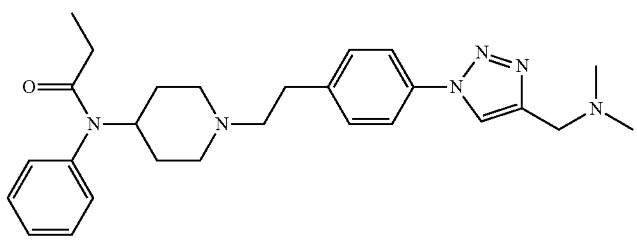 [SMILES: CCC(=O)N(c1ccccc1)C1CCN(CCc2ccc(-n3cc(CN(C)C)nn3)cc2)CC1] | 57.5 | 2.44 | 3.03 | 460.63 | 1.4 | 143 |
| Fen-Tri-OH | 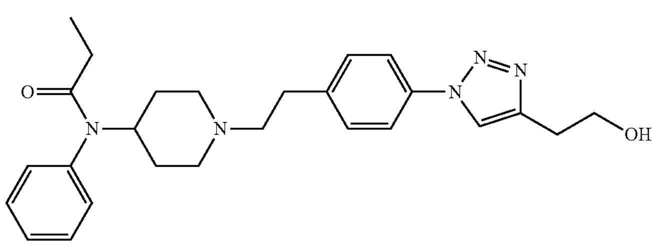 [SMILES: CCC(=O)N(c1ccccc1)C1CCN(CCc2ccc(-n3cc(CCO)nn3)cc2)CC1] | 74.49 | 3.16 | 2.77 | 447.58 | 1.3 | 36 |
| Norfen-Alkyn | 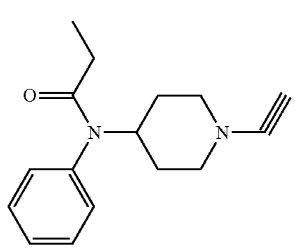 [SMILES: C#CN1CCC(N(C(=O)CC)c2ccccc2)CC1] | 23.55 | 1.00 | 1.94 | 270.38 | 0.8 | n/a |

TABLE 1-continued

| Name | Structure | predicted PSA | PSA/PSA-fentanyl | log P | MW | MW/Fentanyl | EC50 (nM) |
|---|---|---|---|---|---|---|---|
| Norfen-Tri-PEO3 | 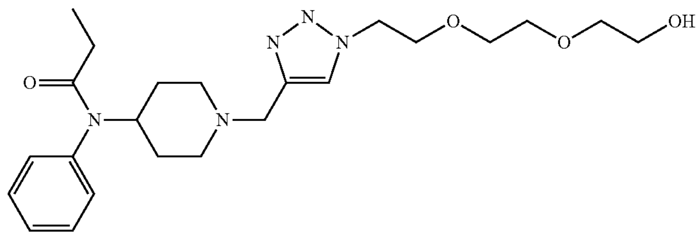 [SMILES: CCC(=O)N(c1ccccc1)C1CCN(CC2=CN(CCOCCOCCO)NN2)CC1] | 92.96 | 3.95 | 0.6 | 445.56 | 1.3 | 62 |
| m-Fen-PO3Et2 | 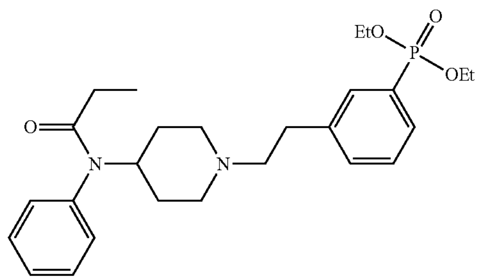 [SMILES: CCOP(=O)(OCC)c1cccc(CCN2CCC(N(C(=O)CC)c3ccccc3)CC2)c1] | 59.09 | 2.51 | 4.1 | 472.57 | 1.4 | 1.3 |
| m-Fen-PO3H2 | 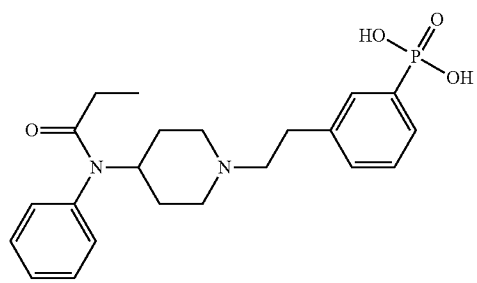 [SMILES: CCC(=O)N(c1ccccc1)C1CCN(CCc2cccc(P(=O)(O)O)c2)CC1] | 81.07 | 3.44 | 3.3 | 416.46 | 1.2 | 22 |
| p-Fen-PO3Et2 | 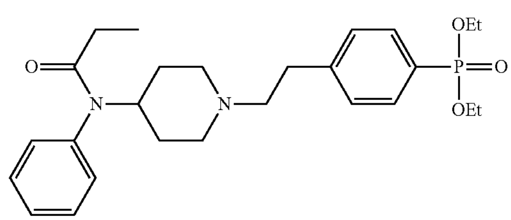 [SMILES: CCOP(=O)(OCC)c1ccc(CCN2CCC(N(C(=O)CC)c3ccccc3)CC2)cc1] | 59.09 | 2.51 | 4.1 | 472.57 | 1.4 | 2 |
| p-Fen-PO3H2 | 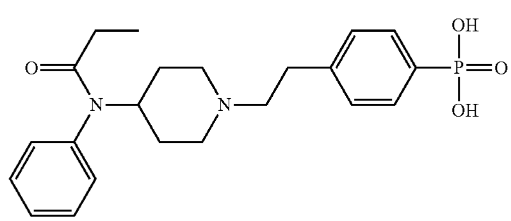 [SMILES: CCC(=O)N(c1ccccc1)C1CCN(CCc2ccc(P(=O)(O)O)cc2)CC1] | 81.07 | 3.44 | 3.3 | 416.46 | 1.2 | 20 |

It is to be understood that the invention or inventions described in this document are not limited to the particular processes, compositions, or methodologies described, as these may vary. It is also to be understood that the terminology used in the description is for the purpose of describing some embodiments, and is not intended to limit the scope of the present disclosure.

The invention claimed is:

1. A compound according to Formula Ia or Formula Ib:

(Ia)
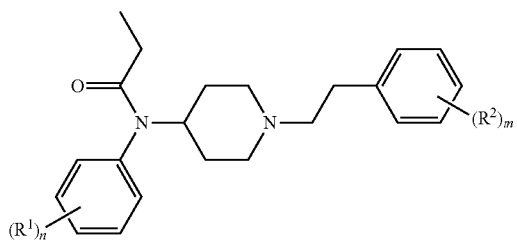

(Ib)
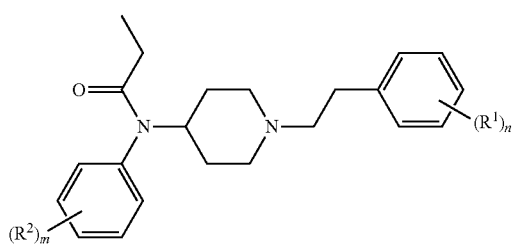

wherein :
each $R^1$ is independently selected from the group consisting of halo, hydroxyl, lower alkyl, amino, carboxyl, and trifluoromethyl;
n is 0, 1 or 2;
m is 1 or 2;
$R^2$ is —(L)$_x$-$R^3$, in which:
x is 1;
L is a linking group selected from the group consisting of —(CH=CH)$_a$-, —(CH=CR)$_b$—, and —C≡C—, wherein:
a is 1, 2 or 3; and
b is 1, 2 or 3;
$R^3$ is —$X^1$—$X^2$—Z,
in which:
$X^1$ is —C(=O)—,
$X^2$ is selected from —O—, and —NH—; and
Z is an oligomer selected from the group consisting of —(CH$_2$CH$_2$—O)$_m$—H, and —(CH$_2$CH$_2$—O)$_m$—CH$_3$ wherein m is from 1 to 20; and
each R is independently selected from H and methyl.

2. A compound according to Formula IIa or Formula IIb:

(Formula IIa)
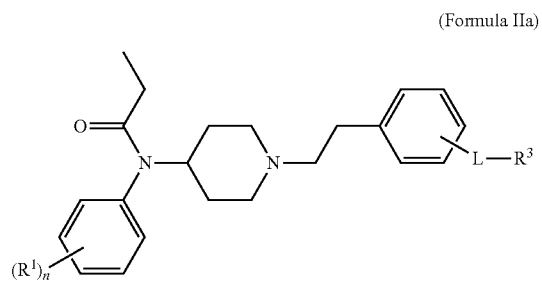

(Formula IIb)
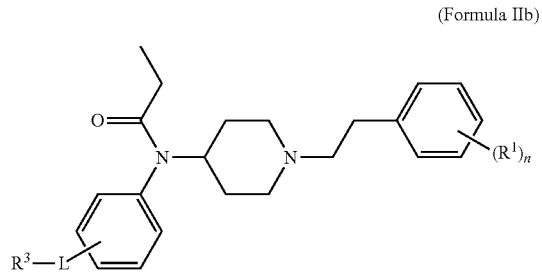

wherein:
each $R^1$ is independently selected from the group consisting of halo, hydroxyl, lower alkyl, amino, carboxyl, and trifluoromethyl;
n is 0, 1 or 2;
L is a linking group selected from the group consisting of —(CH=CH)$_a$-, —(CH=CR)$_b$-, and —C≡C—, wherein:
a is 1, 2 or 3;
b is 1, 2 or 3; and
$R^3$ is —$X^1$—$X^2$—Z,
in which:
$X^1$ is —C(=O)—;
$X^2$ is selected from —O—, and —NH—; and
Z is an oligomer selected from the group consisting of —(CH$_2$CH$_2$—O)$_m$—H, —(CH$_2$CH$_2$—O)$_m$—CH$_3$ and —(CO—CHR—O)$_m$H wherein m is 1 to 20; and
each R is independently selected from H and methyl.

3. The compound according to claim 2, wherein Z is a polyethylene glycol having the formula —(CH$_2$CH$_2$—O)$_m$—H or —(CH$_2$CH$_2$—O)$_m$—CH$_3$, wherein m is from 1 to 16.

4. The compound according to claim 3, having the structure:

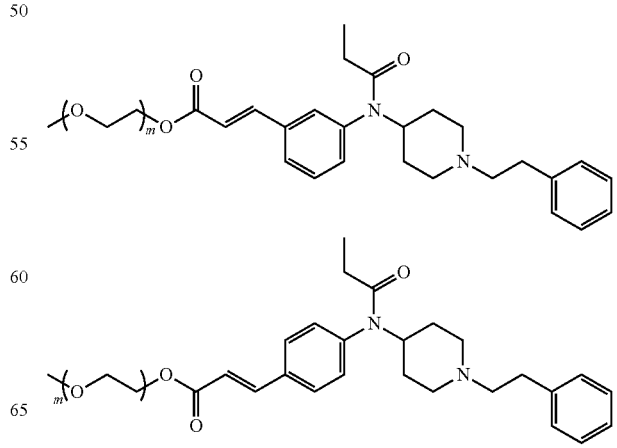

-continued
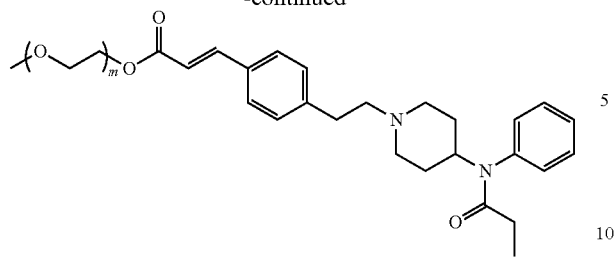
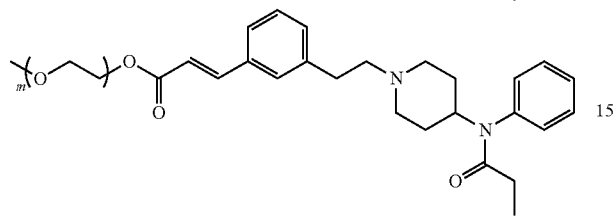
wherein m is a number from 1 to 16.
* * * * *